US 7,879,911 B2

(12) United States Patent
Johnson et al.

(10) Patent No.: US 7,879,911 B2
(45) Date of Patent: Feb. 1, 2011

(54) HYDROXAMIC ACID DERIVATIVES OF PHENOXY-ACETIC ACIDS AND ANALOGS USEFUL AS THERAPEUTIC AGENTS FOR TREATING ANTHRAX POISONING

(76) Inventors: Alan T. Johnson, 45-180 Mahalani Pl. #10, Kaneohe, HI (US) 96744;
Guan-Sheng Jiao, 1702 Kewalo St., #308, Honolulu, HI (US) 96822;
Seongjin Kim, 88 Piikoi St., Apt. 2311, Honolulu, HI (US) 96814

( * ) Notice: Subject to any disclaimer, the term of this patent is extended or adjusted under 35 U.S.C. 154(b) by 240 days.

(21) Appl. No.: 12/011,847

(22) Filed: Jan. 30, 2008

(65) Prior Publication Data
US 2008/0188565 A1 Aug. 7, 2008

Related U.S. Application Data

(60) Provisional application No. 60/898,966, filed on Feb. 1, 2007.

(51) Int. Cl.
| *A61K 31/16* | (2006.01) |
| *A61K 31/165* | (2006.01) |
| *C07C 259/04* | (2006.01) |
| *C07C 259/06* | (2006.01) |
| *C07C 25/13* | (2006.01) |

(52) U.S. Cl. .................. 514/575; 562/621; 570/127
(58) Field of Classification Search ............... 514/575; 562/621; 570/127
See application file for complete search history.

(56) References Cited

U.S. PATENT DOCUMENTS

| 3,517,051 | A | 6/1970 | Bolhofer |
| 6,258,518 | B1 | 7/2001 | Taniguchi |
| 2005/0148629 | A1 | 7/2005 | Xiong |

FOREIGN PATENT DOCUMENTS

| BE | 648892 | 9/1964 |
| FR | 1476525 | 6/1970 |
| JP | 45039246 | 12/1970 |
| JP | 98-99946 | 3/2005 |
| WO | W/O 97/18188 | 5/1997 |
| WO | W/O 97/24117 | 7/1997 |
| WO | W/O 98/38163 | 9/1998 |
| WO | WO 2005/027856 A2 | 3/2005 |

OTHER PUBLICATIONS

Stec et al. Mededelingen Rijksfaculteit Landbouwwetenschappen, Gent 1968, 33(3), 1085-92 (CAS Abstract and structures provided).*
Eckstein, et al.,XP002500542 Database Accession No. 1966:502887, Abstract. See Compounds RN 775-34-8, 13359-17-6.
Venkatesan, et al. J. Med. Chem. 2004, 47(25), 6255-6269. See p. 6256, Table 1, cmpds 9-11 and 14.
Venkatesan et al. J. Med Chem. 2003, 46(12), 2361-2375. See p. 2364, Table 1, cmpds 28, 38 and 39.
Inamasu et al. Database CA XP002500543 Database Accession No. 1976:135326. JP 50 121218 A Sep. 23, 1975. See the Database, Abstract, and Cmpds RN 58835-57-7, 58835-58-8.
Grabowska et al. Database CA XP002500544 Database Accession No. 1969:491012, Roczniki Chemii, 43(4) 715-22, See Database and Abstract p. 718, Table 2 Compounds 25 and 30.
U.S. Appl. No. 12/011,790, filed Jan. 30, 2008, Johnson.
U.S. Appl. No. 12/011,847, filed Jan. 30, 2008, Johnson.
Xiong et al. The discovery of a potent and selective lethal factor inhibitor ". . . ". Bioorg. Med. Chem. Lett. 2006; 16, 964-8. Compound 40, Table 3, p. 4.
Summers et al. Hydroxamic Acid Inhibitors of 5-Lipoxygenase: ". . . ". J. Med. Chem. 1990, 33, 992-998. See Compounds 103-109 found in Table 1 on p. 995.
Boujouklian et al. Ansa Macrolide Synthesis II. A Convergent Approach to Maytansine. Tetrahedron Lett. 1977, 33, 2835-2838.See the intermediate compound 14, p. 2837.
Magnien et al. Substituted 2-Phenoxypropionic and -butyric Acids and Derivatives. J. Med. Chem. 1966, 9, 449-450. See Compounds 3,14,30 and 39, p. 450.

* cited by examiner

*Primary Examiner*—Rebecca L Anderson
*Assistant Examiner*—Jason M Nolan
(74) *Attorney, Agent, or Firm*—Wang, Hartmann, Gibbs & Cawley

(57) ABSTRACT

Compounds having the formula $$HO\underset{H}{\overset{O}{\underset{N}{\|}}}\overset{*}{\underset{R^2}{C}}-X-\text{Ar}(R^1)_m$$

wherein the symbols have the meaning described in the specification are hydroxamic acid derivatives of phenoxy-acetic acids and analogs capable of inhibiting the lethal effects of infection by anthrax bacteria and are useful in the treatment of poisoning by anthrax.

17 Claims, No Drawings

US 7,879,911 B2

HYDROXAMIC ACID DERIVATIVES OF PHENOXY-ACETIC ACIDS AND ANALOGS USEFUL AS THERAPEUTIC AGENTS FOR TREATING ANTHRAX POISONING

CLAIM OF PRIORITY

The present application claims the priority of U.S. provisional application Ser. No. 60/898,966 filed on Feb. 1, 2007.

STATEMENT REGARDING FEDERALLY SPONSORED RESEARCH OR DEVELOPMENT

This invention was made with government support under Grant no. R44AI052587 awarded by the National Institutes of Health. The US government has certain rights in the invention.

BACKGROUND OF THE INVENTION

1. Field of the Invention

The present invention is directed to compounds useful for treatment of poisoning by *bacillus anthracis* (anthrax infection or poisoning). More particularly, the invention is directed to compounds capable of inhibiting the lethal effects of infection by anthrax bacteria and are useful in the treatment of poisoning by anthrax. The compounds of the invention are hydroxamic acid derivatives of phenoxy-acetic acid and its thio, and related analogs.

2. Background Art

Anthrax is a disease caused by infection of mammals, including humans, by *bacillus anthracis*. Spores of these bacteria can enter the mammalian, including human body, through skin abrasions, the digestive system or inhalation. Whereas anthrax poisoning in humans through skin abrasion or the digestive system can often be treated with antibiotics, anthrax poisoning in humans by ingestion of aerosol usually results in death of the infected individual.

Relatively recently, devices have been made which incorporate *bacillus anthracis* or its spores and are capable of releasing the bacteria or its spores in aerosol form. This "weaponized" form of anthrax can serve as a "weapon of mass destruction" in biological warfare and is feared in the Western World for its potential use by terrorists against civilian populations.

For all these reasons a serious effort has been made in the fields of medical and related biological research to elucidate the mode and agent of poisoning by *bacillus anthracis* and efforts have been made to synthesize compounds which act as inhibitors of the lethal toxins and therefore can treat the infection.

The following scientific publications describe or relate to the manner of infection by the bacteria and to elucidation of the toxic factors and their mode of action in the mammalian, including human body: Dixon et al. (1999) N. England J. Med. 341. 815-26; Mock et al. Annu. Rev. Microbiol. 55. 647-71; Vitalae et al. (1998) Biochem. Biopphys. Res. Commun. 248, 706-11; Vitalae et al. (2000) Biochem J. 352 Pt 3, 739-45; Duesbery et al. (1998) Science 280. 734-7; Duesbery et al. International Publication No. WO 99/50439; Hammond et al. (1998) Infect. Immun. 66, 2374-8. A summary of these findings is that the toxin, called "lethal factor", released by *bacillus anthraci* is an enzyme that splits an essential peptide needed by mammalian organisms for signal transmission. Thus, inhibitors of this bacterial enzyme are candidates for drugs for treatment of anthrax poisoning.

Published US Patent Application No. 2005/0148629 (Jul. 7, 2005) describes hydroxamic acid compounds which have the general formula shown below $$HO\underset{H}{\overset{}{N}}\overset{O}{\underset{}{\|}}\underset{R}{\overset{}{C}}\underset{H}{\overset{}{N}}\overset{}{\underset{O}{\overset{O}{\|}}}\underset{O}{\overset{}{S}}R^1$$

where the $R^1$ is aryl, or heteroaryl, or heterocyclic and where R represents a large number of potential substituents, including alkyl, and which can be used in the treatment of anthrax poisoning.

Published International Application WO 2005/027856 (Mar. 31, 2005) describe numerous compounds said to be inhibitors of anthrax lethal factor.

Published International Application WO 97/24117 discloses compounds of the general formula $$HO\underset{H}{\overset{}{N}}\overset{O}{\underset{}{\|}}\underset{R_1\ R_2}{\overset{R_3\ R_4}{(C)_p}}(S(O)_n)_q\underset{}{\overset{R_5\ R_6}{(C)_m}}Ar$$

including some examples where the variable p=1, q=0 and m=1. Said compounds are said to be inhibitors of cyclic AMP phosphodiesterase.

Published European Patent Application EP 1 707 560 A1 includes formulas 1 through 10 (pages 1-15) which purport to cover a very large number of compounds of diverging structures, some of which are pertinent to the compounds of the present invention.

The present invention represents a further advance in the field by providing hydroxamic acid derivatives of phenoxy-acetic acid and analogs which are useful to treat anthrax poisoning.

SUMMARY OF THE INVENTION

The present invention relates to compounds of Formula 1

$$HO\underset{H}{\overset{}{N}}\overset{O}{\underset{}{\|}}\underset{R^2}{\overset{*}{C}}X\underset{}{\overset{}{\bigcirc}}(R^1)_m$$

Formula 1 where
  X is O, S, SO or $SO_2$;
  $R^1$ is F, Cl, Br, I, alkyl of 1-3 carbons, alkoxy of 1-3 carbons, thioalkoxy of 1-3 carbons, phenyl, O-phenyl, CN, $CF_3$, $OCF_3$, OH, $NH_2$, $NHC_1$-$C_6$alkyl, $N(C_1$-$C_6$alkyl$)_2$, COOH or COO($C_1$-$C_6$alkyl);

m is an integer having the value of 1 to 3;
  $R^2$ is alkyl of 1-6 carbons; $C_1$-$C_6$ alkylphenyl where phenyl is substituted with 0-3 $R^1$ groups, $C_2$-$C_6$alkenylO(CH$_2$)$_n$phenyl where alkenyl has 2 to 6 carbons and one double bond and phenyl is substituted with 0-3 $R^1$ groups, $C_1$-$C_6$ alkylcyclohexyl, $(CH_2)_nOR^3$, $(CH_2)_nNHR^4$, $NR^4C_1-C_6alkyl$, $(CH_2)_n CF_3$, $CH_2OCH_2phenyl$; $(CH_2)_nNH(CH_2)_nR^4$, $(CH_2)_n NR^6R^4$, $(CH_2)_n NR^6(CH_2)_nR^4$, $(CH_2)_nO(CH_2)_nR^4$, $(CH_2)_n OR^4$, n is an integer having the value of 1 to 8;

$R^3$ is H, alkyl of 1 to 6 carbons, alkylphenyl where the alkylgroup has 1 to 6 carbons and the phenyl is substituted with 0-3 $R^1$ groups;

$R^4$ is H, cyclohexyl, C(O)alkyl of 1 to 4 carbons, C(O) alkylphenyl where the alkylgroup has 1 to 4 carbons and the phenyl is substituted with 0-3 $R^1$ groups or with a 5 to 6 membered heteroaryl group having 1 to 2 heteroatoms selected from O, S, and N, or with a 5 to 6 membered heteroaryl group having 1 to 2 heteroatoms selected from O, S and N and condensed with a phenylgroup, said heteroaryl or condensed heteroaryl group itself substituted with 0-3 $R^1$ groups, or $R^4$ is $C(O)(CH_2)_pCOOH$, $(CH_2)_p$phenyl where the phenyl is substituted with 0-3 $R^1$ groups or with a $NO_2$ group, or $R^4$ is $C(O)OC_1-C_6alkyl$, or $R^4$ is $CH(CH_3)$phenyl where the phenyl is substituted with 0-3 $R^1$ groups, or $R^4$ is C(O) $(CH_2)_p$phenyl where the phenyl is substituted with 0-3 $R^1$ groups, or $R^4$ is $C(O)CH(Ph)_2$, C(O)—$CH_2$-(3PhO-)Ph, or $R^4$ is a 5 to 6 membered heteroaryl group having 1 to 2 heteroatoms selected from O, S, and N, or a 5 to 6 membered heteroaryl group having 1 to 2 heteroatoms selected from O, S and N and condensed with a phenylgroup, said heteroaryl or condensed heteroaryl group itself substituted with 0-3 $R^1$ groups, or $R^4$ is $CH_2$heteroaryl where the heteroaryl group is 5 or 6 membered and has 1 to 2 heteroatoms selected from O, S, or $R^4$ is $SO_2$-alkyl of 1 to 6 carbons, $SO_2$-Ph where the phenyl is substituted with 0-3 $R^1$ groups or with $NO_2$ or with $COOR^5$ group, or $R^4$ is C(O)NH-alkylphenyl, or C(O)NH-phenyl where the alkyl group has 1 to 4 carbons and where the phenyl is substituted with 0-3 $R^1$ groups;

p is an integer having the value of 0 to 4;

$R^5$ is alkyl of 1 to 6 carbons or phenyl substituted with 0-3 $R^1$ groups or with an OPh group;

$R^6$ is alkyl of 1 to 6 carbons;

the asterisk indicates an asymmetric carbon, the wavy line represents a bond that can be in the R or in the S configuration, or a pharmaceutically acceptable salt of said compound, with the proviso that compounds selected from the group consisting of compounds identified below with structural formulas and designations of the variables $R^1$ where $R^1$ is H, 2-Me, 4-Me, 4-Br, 2-phenyl, 2-(3-propenyl), 4-O-n-Bu, 2-Me-4-Br, 2,4-diCl, 2,4-diBr, 2,5-diCl, 2,4,5-triCl, 2,5-diCl-4-Me, or 2,4-diCl-4-Br, and where $R^1$ is 2-phenyl, 2-(3-propenyl), 2,3-dimethyl, or 2,4-diCl, and where $R^1$ is H, 2-Me, 2-Cl, 2-OMe, 3-Me, 3-Cl, 3-OMe, 3-$CF_3$, 4-OMe, 4-SMe, or 4-phenyl, and are not included in the invention as novel composition of matter.

The present invention also relates to pharmaceutical compositions suitable for administration to mammals, including humans, which include one or more compounds of the invention and are used for treatment or prevention of anthrax poisoning.

Biological Activity, Modes of Administration

Determining Biological Activity

As briefly noted above in the introductory section of this application for patent, the most serious, often lethal results of anthrax poisoning are caused by a toxin that is released by *bacillus anthracis* within the host. The toxin includes three proteins, one of which is a zinc-dependent metalloprotease enzyme (lethal factor) that cleaves near the N termini of several MAP kinase kinase enzymes (MKKs) of the host. It is this disruption of key signaling pathways mediated by the host MKK enzymes that result in the severe and often lethal results of infection by the bacteria.

An assay for identifying and measuring the effectiveness of potential drugs to treat anthrax poisoning is based on measuring the inhibitory effect of the candidate compound on the lethal factor enzyme. The procedure used in the present invention to measure the potential efficiency of the compounds of the present invention is based, in a somewhat modified form, on the assay described by Cummings et al., A peptide-based fluorescence resonance energy transfer assay for *Bacillus anthracis* lethal factor protease, PNAS, May 14, 2002, Vol 99, No. 10 6603-6606, expressly incorporated herein by reference. The gist of this assay that a fluorogenic peptide substrate is incubated with the lethal factor enzyme in the presence of the inhibitor and the inhibition of the lethal factor is measured by measuring the fluorescence intensity of the cleaved substrate. A description of the actual assay conditions used for evaluating the compounds of the present invention is provided below.

Assay Procedure

Inhibitors were solubilized in 100% DMSO at 10 mM, then diluted to the final desired concentration and 10% final DMSO in the assay. Lethal factor protease (20 nM) and inhibitor were briefly incubated at room temperature in the assay buffer (20 mM Hepes, 0.05% Tween 20, 0.02% NaN$_3$, pH 7.4), and the reaction started by the addition of 12.5 μM final of the fluorogenic peptide substrate, MAPKKide™ (List Biological Laboratories, Inc, Campbell, Calif.). The final volume was 50 μL, in half area black microtiter plates (Costar). Fluorescence intensity (Ex: 320 nm, Em: 420 nm) was monitored for 15 minutes at room temperature (Gemini XS, Molecular Devices), and the $K_i^{app}$ values were calculated using the program BatchKi (BioKin Ltd., Pullman, Wash.). Generally speaking a compound is considered active in this assay if the calculated $K_i^{app}$ value is less than 300 (<300) μM.

Modes of Administration

The compounds of the invention are useful for treating anthrax poisoning. The compounds of this invention may be administered systemically through oral, intravenous or other modes of systemic administration, depending on such considerations as the severity of the anthrax infection treated, quantity of drug to be administered, and numerous other considerations. For oral administration the drug may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate the compounds of the invention in suppository form or as extended release formulation for deposit under the skin or intramuscular injection. For each type of administration appropriate pharmaceutical excipients are likely to be added to the drug. The nature of such excipients for each type of systemic administration is well known in the art and need not be described here further.

A useful therapeutic or prophylactic concentration will vary from with the precise identity of the drug, with the severity of the anthrax infection being treated and the patient's susceptibility to treatment. Accordingly, no single concentration will be uniformly useful, but will require modification depending on the particularities of each situation. However, it is anticipated that an amount between 0.1 and 10 mg per kg of body weight per day will effect a therapeutic result.

Results of the Assay Measuring Lethal Factor Inhibitory Activity

Specific examples of compounds within the scope of the present invention are shown by their respective structural formulas in Tables 1 through 3, and their activity in the above-described assay is also indicated.

TABLE 1

| Compound # | X | R$^2$ | LF (FRET) $K_i^{app}$ μM |
|---|---|---|---|
| 167182 | —O— | —H | 29.2 |
| 167163 | —O— | n-Bu | 5.5 |
| 167303 | —S— | n-Bu | 2.5 |

TABLE 1-continued

| Compound # | X | R$^2$ | LF (FRET) $K_i^{app}$ μM |
|---|---|---|---|
| 167316 | —SO— | n-Bu | 18.0 |
| 167351 | syn-SO— | n-Bu | 10.3 |
| 167352 | anti-SO— | n-Bu | 67 |
| 167304 | —SO$_2$— | n-Bu | 30 |

TABLE 2

| Compound # | R$^1$ | R$^2$ | LF (FRET) $K_i^{app}$ μM |
|---|---|---|---|
| 168090 | H | (R) n-Pr | 3.70 |
| 168093 | H | (R) —(CH$_2$)$_2$—OH | 23.1 |
| 168176 | H | (R) —(CH$_2$)$_4$—OH | 1.78 |
| 168142 | H | (R) —(CH$_2$)$_2$—N(Me)—(CH$_2$)$_3$-(3-Me-4-F—Ph) | 1.12 |
| 168143 | H | (S) [piperidine-piperidine group] | 1.67 |
| 168097 | H | (R) —(CH$_2$)$_4$NH—CH$_2$-(3-Me-4-F—Ph) | 0.21 |
| 168100 | Me | (R) —(CH$_2$)$_4$NH—CH$_2$-(3-Me-4-F—Ph) | 0.58 |
| 168178 | H | (R) —(CH$_2$)$_4$NH—CH$_2$-3-(4-F—Ph)Ph | 0.13 |
| 168177 | H | (R) —(CH$_2$)$_4$NH—CH$_2$-2-thienyl | 0.21 |
| 168184 | H | (R) —(CH$_2$)$_4$NH—CH$_2$-2-furanyl | 0.75 |
| 168183 | H | (R) —(CH$_2$)$_4$NH—CH$_2$-2-bicyclo[2.2.1]heptan-2-yl | 0.17 |
| 168185 | H | (R),(E) —CH$_2$—CH=CH—CH$_2$—OCH$_2$Ph | 0.77 |
| 168101 | H | (R) —(CH$_2$)$_4$—OCH$_2$Ph | 1.48 |
| 168113 | H | (R) —(CH$_2$)$_4$—OCH$_2$-(3-Me-4-F—Ph) | 0.54 |
| 168135 | Me | (R) —(CH$_2$)$_4$—OCH$_2$-(3-Me-4-F—Ph) | 3.03 |

TABLE 3

| Compound # | Ar | LF (FRET) $K_i^{app}$ μM |
|---|---|---|
| 168128 | 4-F—Ph— | 61.1 |
| 168129 | 4-Cl—Ph— | 83.9 |
| 168130 | 3,4-diF—Ph— | 26.2 |
| 168127 | 3-Cl-4-F—Ph— | 31.2 |
| 168115 | 3,5-diMe-4-F—Ph— | 2.52 |

TABLE 4

[Structure: HO-NH-C(=O)-CH(R²)-O-phenyl(3-Cl, 4-F)]

| Compound # | R² | LF (FRET) $K_i^{app}$ μM |
|---|---|---|
| 168160 | (E) —CH$_2$—CH═CH—CH$_2$—OCH$_2$Ph | 1.25 |
| 168187 | —(CH$_2$)$_4$—OCH$_2$Ph | 1.07 |

GENERAL EMBODIMENTS AND SYNTHETIC METHODOLOGY

Definitions

The term alkyl refers to and covers any and all groups which are known as normal alkyl and branched-chain alkyl. Unless specified otherwise, lower alkyl means the above-defined broad definition of alkyl groups having 1 to 6 carbons in case of normal lower alkyl, and 3 to 6 carbons for lower branch chained alkyl groups. A pharmaceutically acceptable salt may be prepared for any compound used in accordance with the invention having a functionality capable of forming a salt, for example an acid or an amino functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids. Preferred salts are those formed with inorganic acids such as hydrochloric acid, sulfuric acid or phosphoric acid. Any of a number of simple organic acids such as mono-, di- or tri-acid may also be used.

Some compounds used in accordance with the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds used in accordance with the present invention may contain one or more chiral centers and therefore may exist in enantiomeric and diastereomeric forms. The scope of the present invention is intended to cover all isomers per se, as well as mixtures of cis and trans isomers, mixtures of diastereomers, pure enantiomers (optical isomers) and 50:50 (racemic) or other ratio mixtures of enantiomers as well. In some cases one compound of a diastereomeric species, or one specific enantiomer of a chiral compound is more active than the other diastereomer(s) or optical isomer, and when such a case is established it is indicated in the respective designation of the compound.

General Synthetic Methodology

The novel compounds used in accordance with the invention are encompassed by the general Formula 1 provided above.

A general route for the synthesis of the compounds of Formula 1 where the variable X is O is shown in the General Scheme 1, below.

Referring now to General Scheme 1 a derivative of an alpha-bromo acetic acid ester (such as for example 1-bromo hexanoic acid methyl ester) and a substituted phenol serve as starting materials. The variables R$^1$, m and R$^2$ are as defined in Formula 1. Such starting materials are either available commercially or can be obtained in accordance with known chemical scientific and or patent literature or by such modifications of known synthetic procedures which will be readily apparent to those skilled in the art. The alpha-bromo acetic acid ester derivative and the substituted phenol are reacted in a suitable solvent, such as dimethylformamide (DMF) in the presence of an acid acceptor, such as potassium carbonate to give the compound shown in the scheme as Intermediate Formula 1. Intermediate Formula 1 is reacted with hydroxylamine hydrochloride in the presence of potassium cyanide in a suitable solvent such as mixture of tetrahydrofuran (THF) and methanol (MeOH) to give the compounds of Formula 2. The compounds of Formula 2 are in the scope of the present invention and represent a subgenus of the compounds of Formula 1.

A general route for the synthesis of the compounds of Formula 1 where the variable X is S is shown in the General Scheme 2, below. The steps of this scheme are analogous to the steps of General Scheme 1 except that one starting material is a substituted thiophenol instead of the substituted phenol of the first scheme. The resulting compounds of Formula 3 are in the scope of the present invention and represent a subgenus of the compounds of Formula 1.

A general route for the synthesis of the compounds of Formula 1 where the variable X is SO$_2$ is shown in the General Scheme 3, below. In accordance with this scheme the Intermediate of Formula 2 is oxidized with a strong oxidizing agent, such as the commercially available proprietary reagent known as Oxone® (potassium peroxymonosulfate) to provide the sulfone shown as Intermediate Formula 3. Other suitable oxidizing agents for this latter reaction are hydrogen peroxide or m-chloroperbenzoic acid. Intermediate Formula 3 is then reacted with hydroxylamine hydrochloride in the presence of potassium cyanide in a mixture of tetrahydrofuran (THF) and methanol (MeOH) to give the compounds of Formula 4. The compounds of Formula 4 are in the scope of the present invention and represent a subgenus of the compounds of Formula 1.

A general route for the synthesis of the compounds of Formula 1 where the variable X is SO is shown in the General Scheme 4, below. In accordance with this scheme the Intermediate of Formula 2 is oxidized with hydrogen peroxide (H$_2$O$_2$ 30% solution) in a solvent such as methanol. The resulting sulfoxide isomers of syn and anti configuration (Intermediate of Formula 4) are reacted with hydroxylamine hydrochloride in the presence of potassium cyanide in a mixture of tetrahydrofuran (THF) and methanol (MeOH) to give the compounds of Formula 5 (syn and anti configuration). The compounds of Formula 5 are in the scope of the present invention and represent a subgenus of the compounds of Formula 1.

General Synthetic Scheme 1

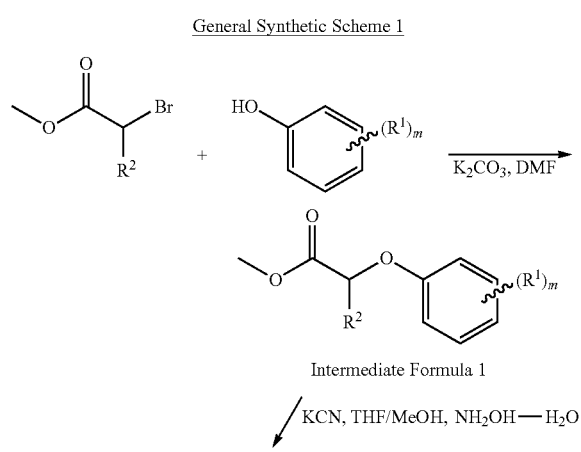

Formula 2

General Synthetic Scheme 2

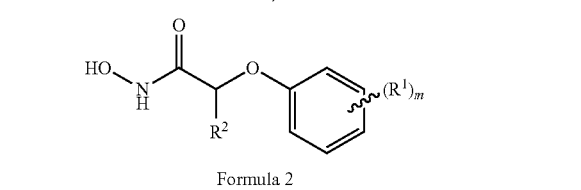

Formula 3

General Synthetic Scheme 3

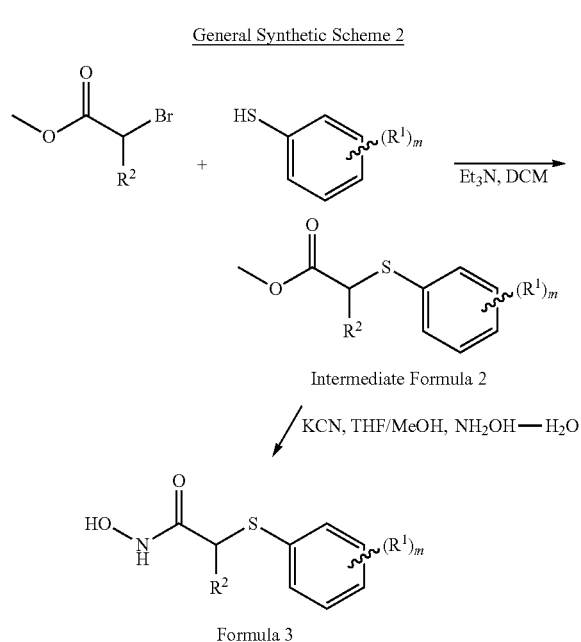

Intermediate Formula 2

-continued

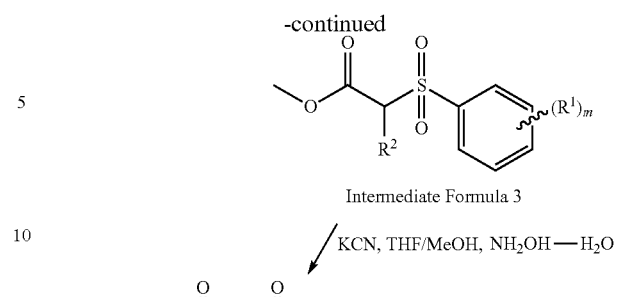

Formula 4

General Synthetic Scheme 4

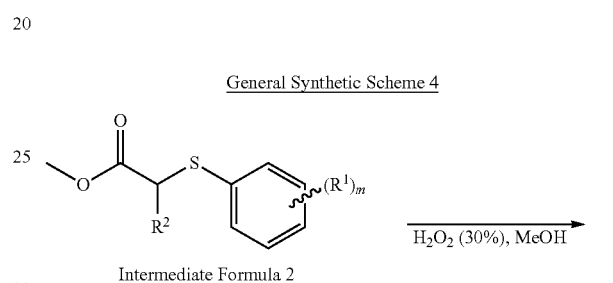

Formula 5

General Scheme 5 discloses a synthetic route for the preparation of compounds of the invention where the variable X is O, and $R^2$ is $(CH_2)_nNHR^4$ and $R^4$ is $(CH_2)_p$phenyl with the phenyl substituted in the manner described in connection with Formula 1. One starting material in this scheme is bromo-acetic acid ethyl (methyl or other alkyl) ester and the other is a phenol substituted with 0 to 3 $R^1$ groups. The variable $R^1$ is defined as in connection with Formula 1. Generally speaking, in the description of these synthetic schemes, unless otherwise indicated the variables are defined as in connection with Formula 1. The two starting materials are reacted in the presence of strong base, such as KOH to pride a phenoxyacetic acid derivative of Intermediate Formula 6. Intermediate Formula 6 is then converted to the corresponding acid chloride by treatment with phosgene ($COCl_2$) in a suitable solvent or solvent mixture, such as DMF and DCM. The acid chloride of Intermediate Formula 7 is then reacted with (S)-(4)-isopropyl-2-oxazolidinone (available from commercial sources, eg. Aldrich Chemical Co.) in the presence of butyl lithium (BuLi) in an aprotic solvent, such as THF to give Intermediate Formula 8. The Intermediate Formula 8 is then reacted with an allylic halide for example a benzyloxyallyl-iodide derivative, shown in the reaction scheme in the presence of lithium bis(trimethylsilyl)amide (LiHMDS) to provide Intermediate Formula 9. The benzyl protective group of the Intermediate Formula 9 is removed and at the same time the carbon-carbon double bond is reduced by catalytic hydrogenation to give Intermediate Formula 10. The Intermediate Formula 10 is oxidized by treatment with 1,1,1-tris(acetoxy)-1,1-dihydro-1,2-benziodoxol-3-(1H)-one (Dess-Martin periodinane reagent) in dichloromethane to give the aldehyde compound of Intermediate Formula 11. The Intermediate Formula 11 is then reacted with a phenylalkylamine shown in the scheme to first provide a Schiff base compound that is reduced by treatment with sodium triacetoxyborohydride (NaBH(OAc)$_3$) to give Intermediate Formula 12. The Intermediate Formula 12 is then reacted with hydroxylamine hydrochloride in the presence of potassium cyanide in a mixture of tetrahydrofuran (THF) and methanol (MeOH) to give the compounds of Formula 6. The compounds of Formula 6 are in the scope of the present invention and represent a subgenus of the compounds of Formula 1.

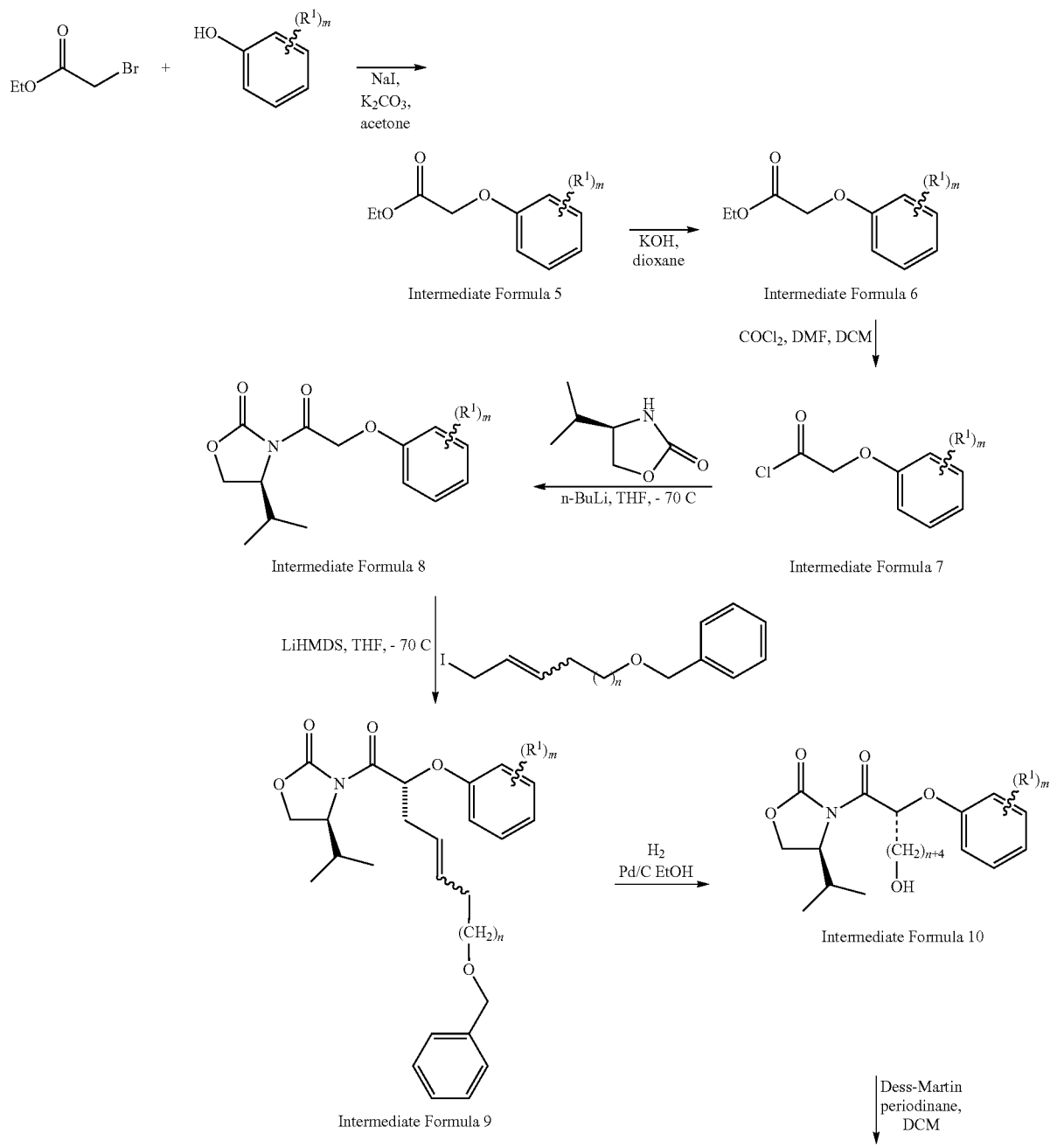

General Synthetic Scheme 5

-continued

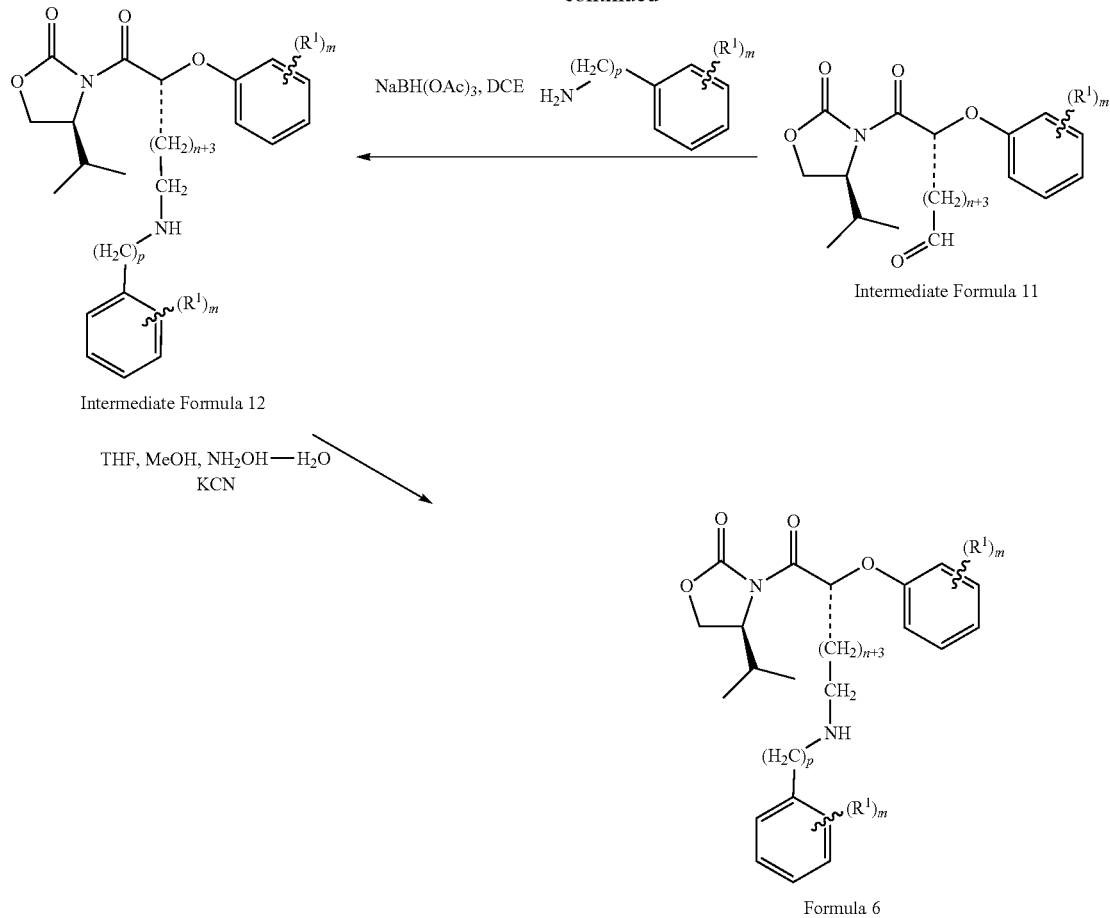

Intermediate Formula 12

Intermediate Formula 11

Formula 6

General Scheme 6 discloses a synthetic route for the preparation of compounds of the invention where the variable X is O, and $R^2$ is $(CH_2)_4OR^4$ and $R^4$ is $(CH_2)_p$phenyl with the phenyl substituted in the manner described in connection with Formula 1. One starting material in this scheme is 1,4-dihydroxy-2-butene, and the other is a 1-bromo-omega-phenyl substituted with 0 to 3 $R^1$ groups. These starting materials are either available commercially or from the chemical scientific and patent literature, or by such modification of the known procedures that will be readily apparent to those skilled in the art. The two starting materials are reacted in the presence of sodium hydride in an aprotic solvent, such as THF, to give Intermediate Formula 13. The Intermediate Formula 13 is then reacted with tripehylphosphine and iodine to give the iodo compound of Intermediate Formula 14. The Intermediate Formula 14 is reacted with a (S)-(3 phenoxy) acetyl-4-isopropyloxazolidine-2-one (Intermediate Formula 8 in General Scheme 5) to provide Intermediate Formula 15. The olefinic bond of the compound of Intermediate Formula 15 is removed by hydrogenation to give Intermediate Formula 16. The Intermediate Formula 16 is converted by treatment with hydroxylamine hydrochloride in the presence of potassium cyanide in a mixture of tetrahydrofuran (THF) and methanol (MeOH) to the compounds of Formula 7. The compounds of Formula 7 are in the scope of the present invention and represent a subgenus of the compounds of Formula 1.

General Synthetic Scheme 6

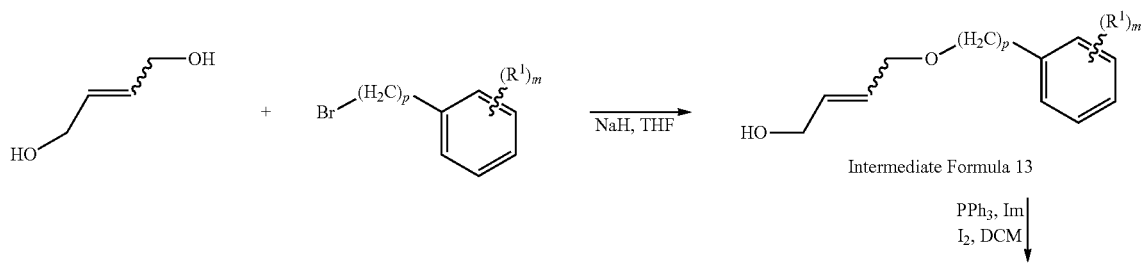

Intermediate Formula 13

PPh₃, Im
I₂, DCM

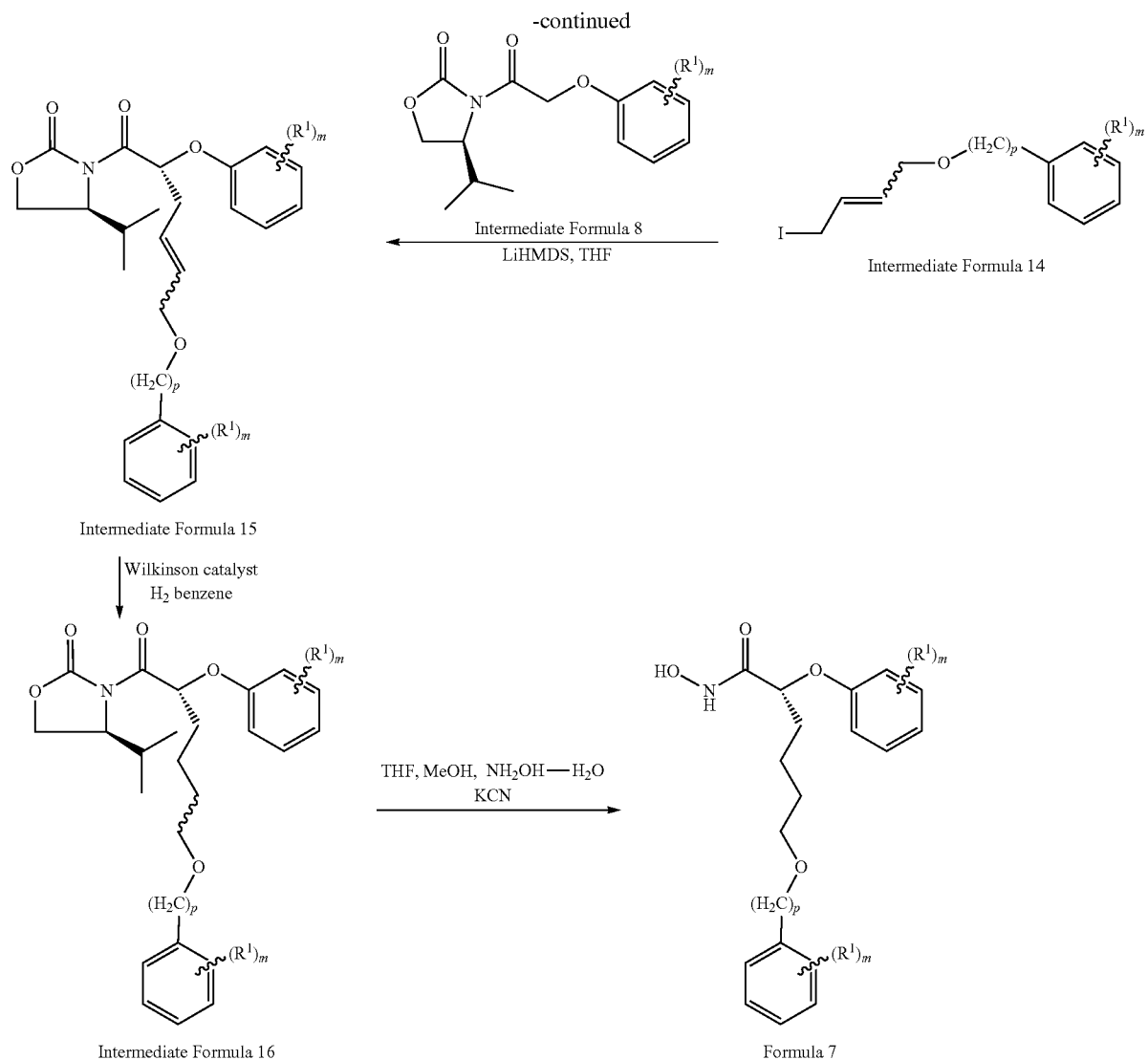

Intermediate Formula 15

Intermediate Formula 16

Formula 7

Intermediate Formula 14

General Scheme 7 discloses another synthetic route for the preparation of compounds of the invention where the variable X is O, and $R^2$ is $(CH_2)_nNR^6R^4$ and $R^4$ is $(CH_2)_p$phenyl with the phenyl substituted in the manner described in connection with Formula 1, and where the variable p is greater than one (1). The scheme is actually shown for making of compounds of the invention where p represents the integer three (3) and $R^6$ is methyl. However, a person of ordinary skill in the art of synthetic organic chemistry would be readily able to modify the disclosure of General Scheme 7 to prepare compounds within the scope of this disclosure where $R^6$ is other than methyl, and the variable p is an integer other than three (3).

The staring material in this scheme is a 2-phenoxyacetyl chloride where the phenyl group is substituted with 0 to 3 $R^1$ groups. This starting material is either available commercially or from the chemical scientific and patent literature, or by such modification of the known procedures that will be readily apparent to those skilled in the art. The starting material is reacted with (S)-4-benzyl-2-oxazolidinone (available from commercial sources) in the presence of n-butyl lithium in an aprotic solvent, such as THF, to give Intermediate Formula 17. The Intermediate Formula 17 is reacted with allyl iodide of the formula shown in the reaction scheme in the presence of LiHMDS in an aprotic solvent, such as THF, to provide Intermediate Formula 18. The olefinic bond of the Intermediate Formula 18 is broken by oxidation with ozone and the resulting intermediate ozonide is decomposed by the addition of triphenylphosphine to give the aldehyde compound of Intermediate Formula 19. The Intermediate Formula 19 is reacted with an N-methyl-N-alkylphenylamine such as 3-phenyl-N-methylpropan-1-amine where n=3 and the phenyl group is substituted with 0 to 3 $R^1$ groups to give an intermediate imine (not shown in the scheme) that is then reduced with $NaBH(OAc)_3$ provide Intermediate Formula 20. An example for a reagent of the latter formula and one that is utilized for the preparation of preferred compounds of the invention is 4-fluoro-3-methylphenyl)-N-methylpropan-1-amine. A specific route for the synthesis of 4-fluoro-3-methylphenyl)-N-methylpropan-1-amine is disclosed below in Specific Scheme 7. Those having ordinary skill in the art can readily modify the disclosure of Specific Scheme 7 to obtain other N-methyl-N-alkylphenylamine compounds where n=0 to 6 and the phenyl group is substituted with 0 to 3 R¹ groups. Intermediate Formula 20 is reacted with hydroxylamine hydrochloride in the presence of potassium cyanide in a mixture of tetrahydrofuran (THF) and methanol (MeOH) to the compounds of Formula 8. The compounds of Formula 8 are in the scope of the present invention and represent a subgenus of the compounds of Formula 1.

variable m is preferably the integer selected from 1, 2 and 3. Even more preferably the variable m is 2 or 3. Particularly preferred are compounds of the invention where m is 2, and the R¹ are methyl and fluoro, with the methyl group being in the 3 (meta) position and the fluoro being in the 4 (para) position relative to the X group. Also particularly preferred

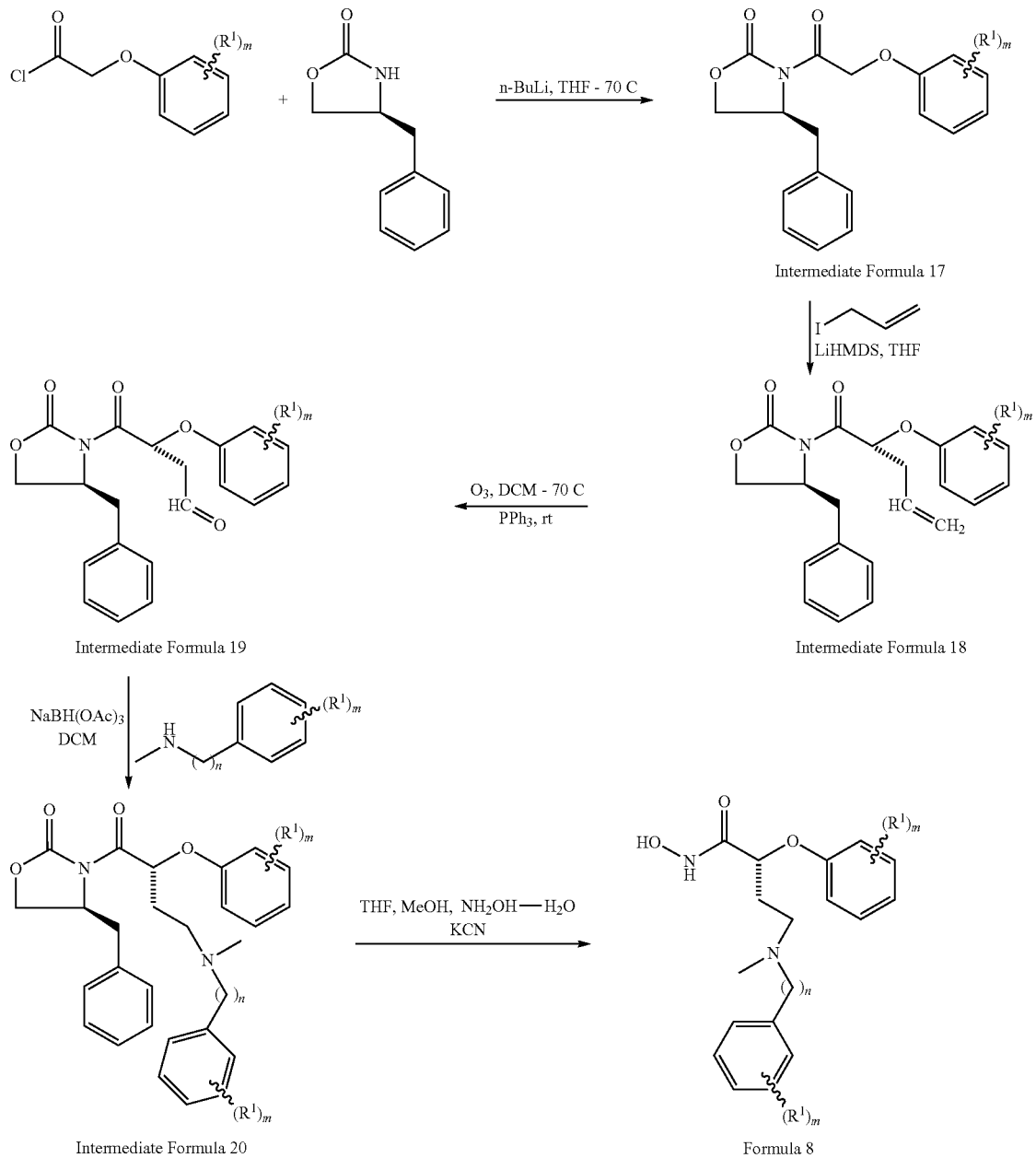

Preferred Examples

Referring now to the variable R¹ in Formula 1, in the compounds of the invention R¹ represents a substituent on the phenyl group shown in the formula. In the preferred compounds of the invention R¹ is F, Cl, methyl, or methoxy. The are compounds where m is 3, and there is a methyl group in the 3,5 (meta, meta) positions and a fluoro in the 4 (para) position of the phenyl ring.

In most of the preferred compounds of the invention the variable X is O or S, with O being preferred over S.

Referring now to the variable $R^2$ in Formula 1 in the preferred compounds of the invention $R^2$ is H, alkyl of 1 to 4 carbons, cyclohexyl, alkylphenyl where the alkyl group has 1 to 3 carbons, $CH_2OCH_2$-phenyl, $(CH_2)_nCF_3$ where n is 2 or 3, $CH_2OR^3$ where $R_3$ is H or t-butyl.

Compounds of the invention are also preferred where the variable $R^2$ is $(CH_2)_nNHR^4$, $(CH_2)_nOR^4$ and $(CH_2)_nNR^6$ $(CH_2)_pR^4$ where n is the integer 3, 4 or p is 3, 5 and $R^4$ is H, $C(O)CH_3$, $C(O)$ substituted phenyl, $CH_2$-phenyl, $CH_2$-thienyl, $CH_2$furanyl, where the phenyl group is substituted with the preferred examples of the $R^1$ group or with a phenoxy group, $C(O)CH_2$-phenyl, $CH(phenyl)_2$, $C(O)(CH_2)_2COOH$, dimethyl substituted pyrrolyl, $SO_2$alkyl of 1 to 3 carbons, $SO_2$phenyl where the phenyl is substituted with the preferred examples of $R^1$ or with a nitro ($NO_2$) group. Still preferred are compounds where $R^4$ is $C(O)NH$-alkylphenyl where the alkyl group has 1 to 4 carbons and the phenyl group is substituted with the preferred examples of the $R^1$ group.

The most preferred compounds of the invention are shown in Tables 1 through 4 above and in the experimental description below.

Experimental

Reaction schemes and experimental description of the synthesis of the presently most preferred compounds of the invention are provided below. The LC/MS data given was obtained using the following conditions: LC/MSD/ELSD analysis performed in ESI positive mode with an Agilent 1100 LC/MSD VL system equipped with Agilent 1100 HP PDA and Sedex 75 ELSD detectors. Column: Zorbax Eclipse SD-C18, 5 μm, 4.6×75 mm; Temperature set at 25° C.; Mobile Phase: % A=0.025% trifluoroacetic acid-water, % B=0.025% trifluoroacetic acid-acetonitrile; or % A=0.10% formic acid-water, % B=0.10% formic acid-acetonitrile; Linear Gradient: 20%-98% B in 15 min.; Flow rate: 1.0 mL/min.; ELSD gain set@3; UV set at 254 nm and 214 nm.

Specific Scheme 1

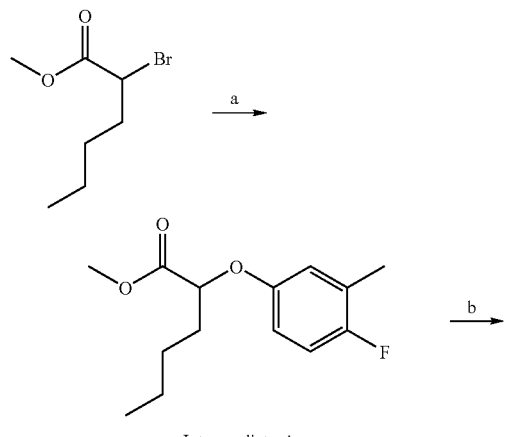

Intermediate A

Compound 167163

Reagents and conditions: (a) 1 eq of 4-fluoro-3-methylphenol, 5 eq of $K_2CO_3$, DMF, rt; (b) KCN (5 mol %), THF/MeOH/50% $NH_2OH$—$H_2O$ (2:2:1), rt.

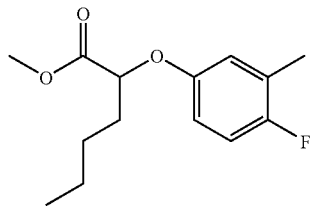

2-(4-Fluoro-3-methyl-phenoxy)-hexanoic acid methyl ester (Intermediate A)

To a solution of 2-bromo-hexanoic acid methyl ester (0.500 g, 2.404 mmol) and 4-fluoro-3-methylphenol (0.303 g, 2.404 mmol) in 15 mL of DMF, was added $K_2CO_3$ (1.661 g, 12.020 mmol). After stirring at room temperature under $N_2$ for 88 h, the reaction mixture was diluted with 60 mL of water and extracted with dichloromethane (60 mL×3). The organic extracts were combined and dried over anhydrous $Na_2SO_4$. After removing the solvent under reduced pressure, the product was isolated by Flash chromatography (silica gel) eluting with 0-20% ethyl acetate/hexanes to give the title compound as yellow oil (0.467 g, 76% yield). LC-MS: $t_R$=10.5 min; m/z 255 (M+H)$^+$.

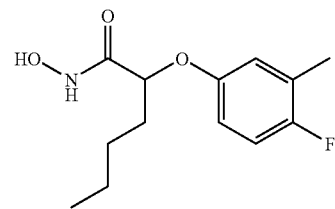

2-(4-Fluoro-3-methyl-phenoxy)-hexanoic acid hydroxyamide (Compound 167163)

To a solution of 2-(4-fluoro-3-methyl-phenoxy)-hexanoic acid methyl ester (0.467 g, 1.838 mmol) in 5 mL of THF/MeOH/50% $NH_2OH$—$H_2O$ (2:2:1), was added KCN (0.006 g, 0.092 mmol). After stirring at room temperature for 15 h, the reaction mixture was diluted with 60 mL of water and extracted with ethyl acetate (60 mL×3). The organic extracts were combined and dried over anhydrous $Na_2SO_4$. After removing the solvent under reduced pressure, the product was isolated by Flash chromatography (silica gel) eluting with 0-10% methanol/dichloromethane to give the title compound a white solid (0.286 g, 61% yield). LC-MS: $t_R$=6.9 min, m/z 256 (M+H)$^+$; $^1$H NMR (300 MHz, $CD_3OD$) δ 0.92 (t, J=6.90 Hz, 3H), 1.32-1.50 (m, 4H), 1.86-1.93 (m, 2H), 2.21 (d, J=1.80 Hz, 3H), 4.50 (t, J=6.00 Hz, 1H), 6.72-6.77 (m, 1H), 6.80-6.83 (m, 1H), 6.91 (t, J=9.00 Hz, 1H).

Specific Scheme 2

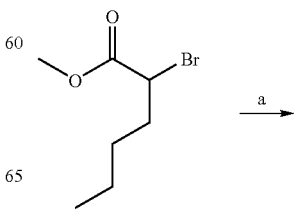

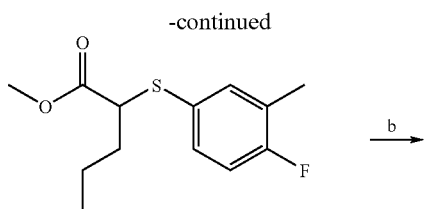

Intermediate A2

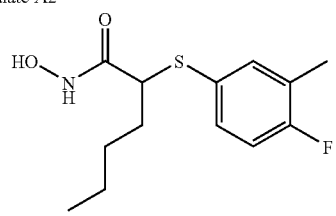

Compound 167303

Reagents and conditions: (a) 1 eq of 4-fluoro-3-methyl-benzenethiol, 10 eq of Et₃N, DCM, rt; (b) KCN (5 mol %), THF/MeOH/50% NH₂OH—H₂O (2:2:1), rt.

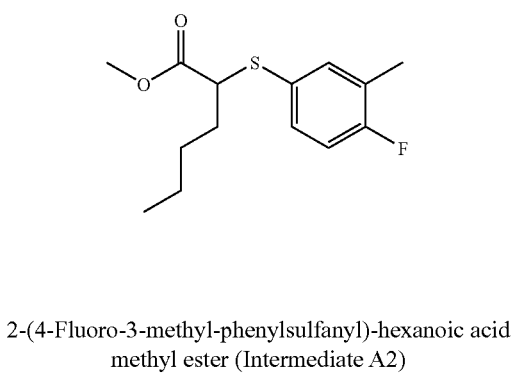

2-(4-Fluoro-3-methyl-phenylsulfanyl)-hexanoic acid methyl ester (Intermediate A2)

To a solution of 2-bromo-hexanoic acid methyl ester (0.500 g, 2.404 mmol) and 4-fluoro-3-methyl-benzenethiol (0.340 g, 2.404 mmol) in 20 mL of dichloromethane, was added triethylamine (3.3 mL, 12.020 mmol). After stirring at room temperature under N₂ for 46 h, the reaction mixture was diluted with dichloromethane and washed with 1N HCl and brine. The organic layer dried over anhydrous Na₂SO₄. After removing the solvent under reduced pressure, the product was isolated by Flash chromatography (silica gel) eluting with 0-20% ethyl acetate/hexanes to give the title compound as colorless oil (0.596 g, 92% yield). LC-MS: $t_R$=11.2 min; m/z 271 (M+H)⁺.

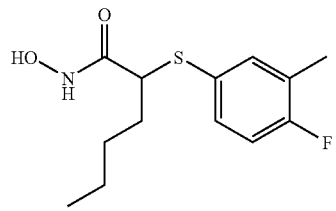

2-(4-Fluoro-3-methyl-phenylsulfanyl)-hexanoic acid hydroxyamide (Compound 167303)

To a solution of 2-(4-fluoro-3-methyl-phenylsulfanyl)-hexanoic acid methyl ester (0.100 g, 0.370 mmol) in 5 mL of THF/MeOH/50% NH₂OH—H₂O (2:2:1), was added KCN (0.002 g, 0.037 mmol). After stirring at room temperature for 64 h, the reaction mixture was diluted with 60 mL of water and extracted with ethyl acetate (60 mL×3). The organic extracts were combined and dried over anhydrous Na₂SO₄. After removing the solvent under reduced pressure, the product was isolated by Flash chromatography (silica gel) eluting with 0-10% methanol/dichloromethane to give the title compound an off-white solid (0.053 g, 53% yield). LC-MS: $t_R$=7.2 min, m/z 272 (M+H)⁺; ¹H NMR (300 MHz, CD₃OD) δ 0.90 (t, J=6.30 Hz, 3H), 1.34-1.35 (m, 4H), 1.65-1.72 (m, 1H), 1.78-1.88 (m, 1H), 2.24 (s, 3H), 3.38 (dd, J=8.70, 6.30 Hz, 1H), 6.99 (t, J=9.00 Hz, 1H), 7.30-7.33 (m, 1H), 7.37 (d, J=6.90 Hz, 1H).

Specific Scheme 3

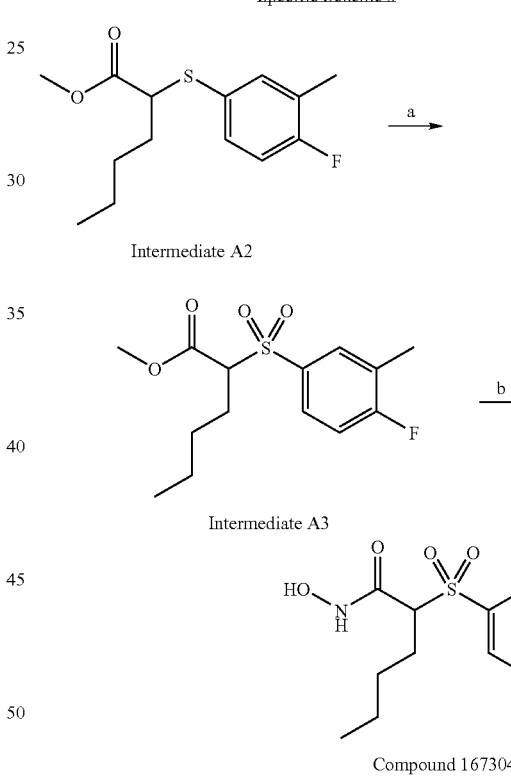

Reagents and conditions: (a) 3 eq of Oxone®, MeOH/H₂O (2:1); (b) KCN (5 mol %), THF/MeOH/50% NH₂OH—H₂O (2:2:1), rt.

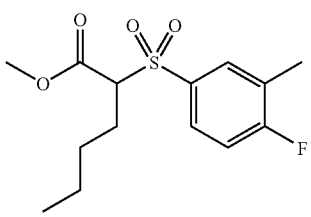

2-(4-Fluoro-3-methyl-benzenesulfonyl)-hexanoic acid methyl ester (Intermediate A3)

To a solution of 2-(4-fluoro-3-methyl-phenylsulfanyl)-hexanoic acid methyl ester (0.160 g, 0.592 mmol) in 15 mL of MeOH/H$_2$O (2:1), was added Oxone® (1.500 g, 1.776 mmol) in portions. After stirring at room temperature for 5 h, the reaction mixture was diluted with 60 mL of water and extracted with dichloromethane (60 mL×3). The organic extracts were combined and dried over anhydrous Na$_2$SO$_4$. After removing the solvent under reduced pressure, the product was isolated by Flash chromatography (silica gel) eluting with 0-30% ethyl acetate/hexanes to give the title compound as colorless semi-solid (0.153 g, 86% yield). LC-MS: t$_R$=9.2 min; m/z 303 (M+H)$^+$.

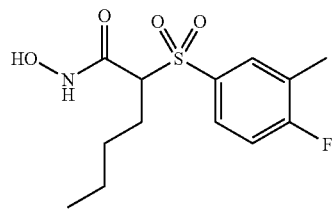

2-(4-Fluoro-3-methyl-benzenesulfonyl)-hexanoic acid hydroxyamide (Compound 167304)

To a solution of 2-(4-fluoro-3-methyl-benzenesulfonyl)-hexanoic acid methyl ester (0.153 g, 0.506 mmol) in 5 mL of THF/MeOH/50% NH$_2$OH—H$_2$O (2:2:1), KCN (0.003 g, 0.051 mmol) was added. After stirring at room temperature for 17 h, the reaction mixture was diluted with 60 mL of water and extracted with ethyl acetate (60 mL×3). The organic extracts were combined and dried over anhydrous Na$_2$SO$_4$. After removing the solvent under reduced pressure, the product was isolated by Flash chromatography (silica gel) eluting with 0-10% methanol/dichloromethane to give the title compound an off-white solid (0.079 g, 52% yield). LC-MS: t$_R$=6.0 min, m/z 304 (M+H)$^+$; $^1$H NMR (300 MHz, CD$_3$OD) δ 0.87 (t, J=6.60 Hz, 3H), 1.22-1.34 (m, 4H), 1.87-1.94 (m, 2H), 2.36 (d, J=1.80 Hz, 3H), 3.72 (dd, J=8.70, 6.60 Hz, 1H), 7.28 (t, J=9.00 Hz, 1H), 7.72-7.75 (m, 1H), 7.78 (d, J=7.20 Hz, 1H).

Specific Scheme 4

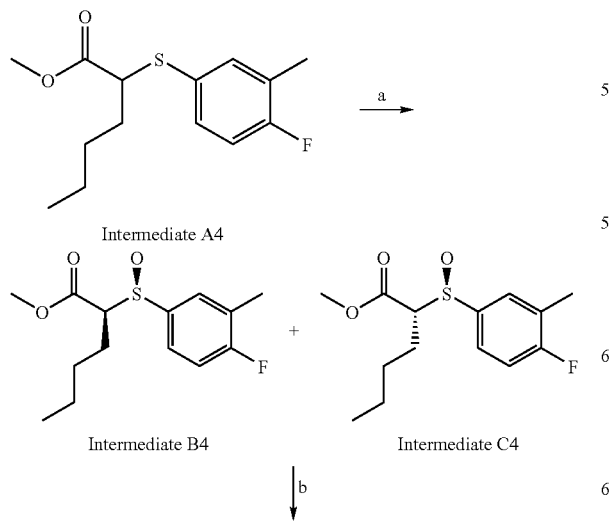

-continued

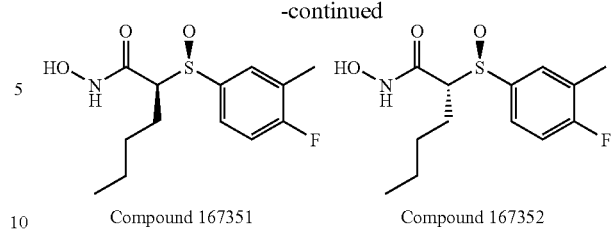

Compound 167351      Compound 167352

Reagents and conditions: (a) H$_2$O$_2$ (30% solution), MeOH; (b) KCN (5 mol %), THF/MeOH/50% NH$_2$OH—H$_2$O (2:2:1), rt.

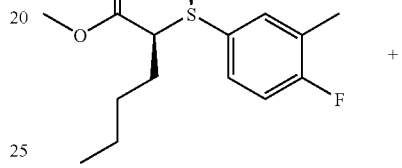

+

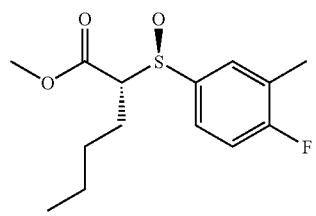

syn-2-(4-Fluoro-3-methyl-benzenesulfinyl)-hexanoic acid methyl ester (Intermediate B4)

anti-2-(4-Fluoro-3-methyl-benzenesulfinyl)-hexanoic acid methyl ester (Intermediate C4)

To a solution of 2-(4-fluoro-3-methyl-phenylsulfanyl)-hexanoic acid methyl ester (Intermediate A4, 0.320 g, 1.185 mmol) in 10 mL of MeOH, was added H$_2$O$_2$ (30%, 2 mL). After stirring at room temperature for 114 h, the reaction mixture was quenched with NaHSO$_3$ solution and extracted with dichloromethane (60 mL×3). The organic extracts were combined and dried over anhydrous Na$_2$SO$_4$. After removing the solvent under reduced pressure, the products were isolated by Flash chromatography (silica gel) eluting with 0-20% ethyl acetate/hexanes to give anti-2-(4-fluoro-3-methyl-benzenesulfinyl)-hexanoic acid methyl ester as colorless oil (fraction 1, 0.145 g, 43% yield, LC-MS: t$_R$=8.4 min; m/z 287 (M+H)$^+$) and syn-2-(4-fluoro-3-methyl-benzenesulfinyl)-hexanoic acid methyl ester as a colorless oil (fraction 2, 0.088 g, 26% yield, LC-MS: t$_R$=8.3 min; m/z 287 (M+H)$^+$).

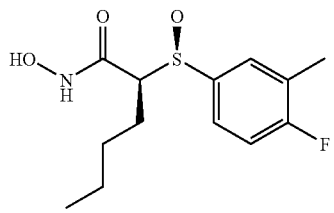

syn-2-(4-Fluoro-3-methyl-benzenesulfinyl)-hexanoic acid hydroxyamide (Compound 167351)

To a solution of cis-2-(4-fluoro-3-methyl-benzenesulfinyl)-hexanoic acid methyl ester (0.088 g, 0.308 mmol) in 5 mL of THF/MeOH/50% NH$_2$OH—H$_2$O (2:2:1), was added KCN (0.002 g, 0.031 mmol). After stirring at room temperature for 24 h, the reaction mixture was diluted with 60 mL of water and extracted with ethyl acetate (60 mL×3). The organic extracts were combined and dried over anhydrous Na$_2$SO$_4$. After removing the solvent under reduced pressure, the product was isolated by Flsh chromatography (silica gel) eluting with 0-10% methanol/dichloromethane to give the title compound an off-white solid (0.048 g, 55% yield). Pure analytic sample was obtained by RP-HPLC purification. LC-MS: $t_R$=4.7 min, m/z 288 (M+H)$^+$; $^1$H NMR (300 MHz, CD$_3$OD) δ 0.92 (t, J=6.59 Hz, 3H), 1.24-1.48 (m, 4H), 2.03-2.05 (m, 2H), 2.34 (s, 3H), 3.22 (dd, J=9.67, 5.27 Hz, 1H), 7.25 (t, J=8.93 Hz, 1H), 7.48-7.51 (m, 1H), 7.54 (d, J=7.03 Hz, 1H).

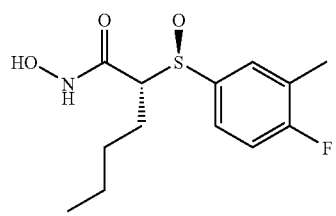

anti-2-(4-Fluoro-3-methyl-benzenesulfinyl)-hexanoic acid hydroxyamide (Compound 167352)

To a solution of trans-2-(4-fluoro-3-methyl-benzenesulfinyl)-hexanoic acid methyl ester (0.145 g, 0.507 mmol) in 5 mL of THF/MeOH/50% NH$_2$OH—H$_2$O (2:2:1), was added KCN (0.003 g, 0.051 mmol). After stirring at room temperature for 24 h, the reaction mixture was diluted with 60 mL of water and extracted with ethyl acetate (60 mL×3). The organic extracts were combined and dried over anhydrous Na$_2$SO$_4$. After removing the solvent under reduced pressure, the product was isolated by Flash chromatography (silica gel) eluting with 0-10% methanol/dichloromethane to give the title compound an off-white solid (0.120 g, 82% yield). Pure analytic sample was obtained by RP-HPLC purification. LC-MS: $t_R$=5.3 min, m/z 288 (M+H)$^+$; $^1$H NMR (300 MHz, CD$_3$OD) δ 0.82 (t, J=6.30 Hz, 3H), 1.10-1.44 (m, 5H), 1.72-1.94 (m, 1H), 2.36 (s, 3H), 3.35 (dd, J=7.91, 3.00 Hz, 1H), 7.28 (t, J=8.93 Hz, 1H), 7.57-7.61 (m, 1H), 7.64 (d, J=6.74 Hz, 1H).

Specific Scheme 5

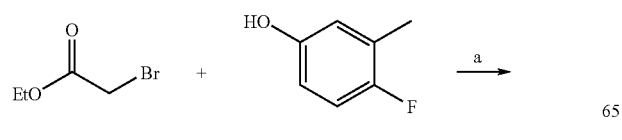

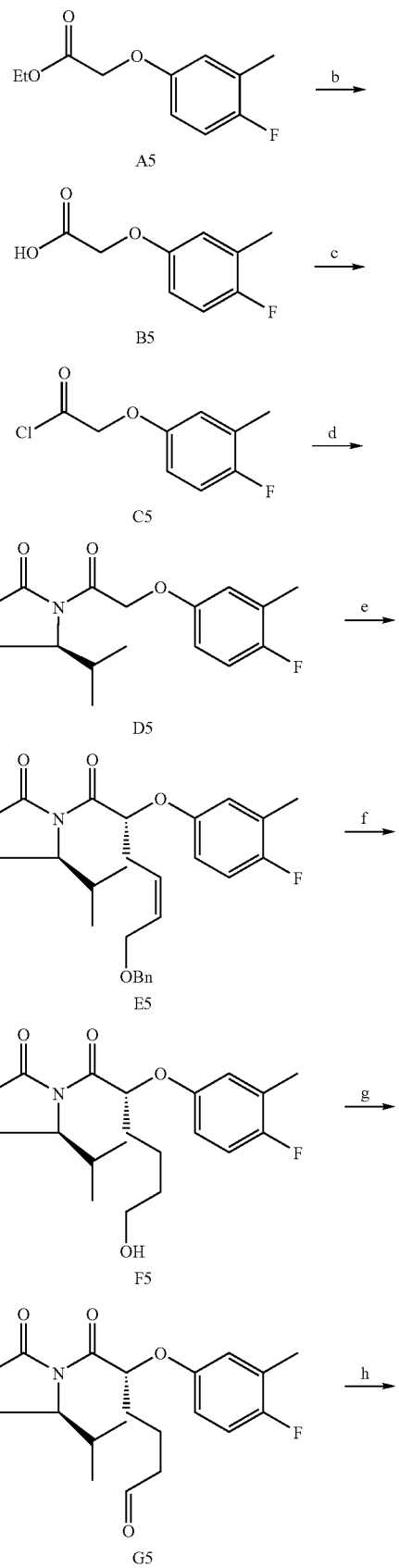

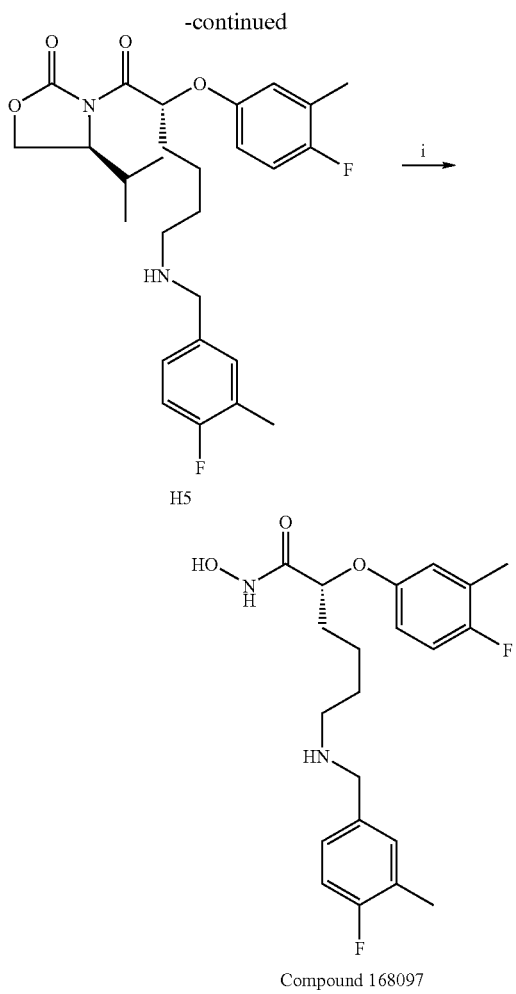

H5

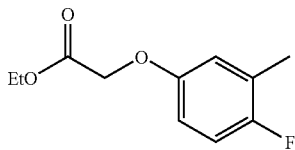

Compound 168097

Reagents and conditions: a) NaI, K$_2$CO$_3$, Acetone, 63° C., 3 h; b) 5% KOH (aq), dioxane, 25° C., 30 min; c) (COCl)$_2$, DMF, DCM, 25° C., 3 h; d) (S)-( )-4-Isopropyl-2-oxazolidinone, n-BuLi, THF, −70° C. to RT, 3 h; e) (4-Iodo-but-2-enyloxymethyl)-benzene, LiHMDS, THF, −70° C. to RT, 3 h; f) 10% Pd/C, H$_2$, EtOH, 25° C., 3 h; g) Dess-Martin periodinane, DCM, 25° C., 3 h; h) 4-Fluoro-3-methyl-benzylamine, NaBH(OAc)$_3$, DCE, 25° C., 8 h; i) NH$_2$—OH, KCN, H$_2$O, MeOH, THF, 25° C., 3 days.

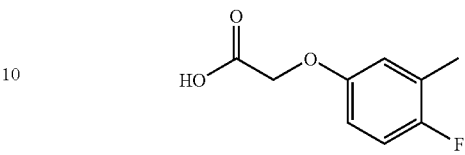

Ethyl 2-(4-fluoro-3-methylphenoxy)acetate (A5)

To a solution of Bromo-acetic acid ethyl ester (1.3 g, 7.1 mmol) and 4-Fluoro-3-methyl-phenol (1.0 g, 7.1 mmol) in 10 mL acetone was added K$_2$CO$_3$ (979 mg, 7.1 mmol) and NaI (7.1 mg, 0.047 mmol) at 25° C. The reaction mixture was stirred for 3 h at 63° C. and the temperature was slowly reduced to room temperature over a period of 30 min. Evaporation of solvent left the crude from which the product was isolated by Flash column chromatography eluting with 0% to 10% ethyl acetate/hexane to give the title compound, 1.1 g, as a light yellow oil.

MS (EI) m/z 212 (M$^+$), 84 (M−128) base peak.

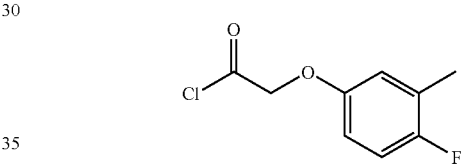

2-(4-Fluoro-3-methylphenoxy)acetic acid (B5)

To the solution of ethyl 2-(4-fluoro-3-methylphenoxy)acetate (1.1 g, 5.1 mmol) in 10 mL dioxane was added 10 mL aqueous 5% KOH at 25° C. After being stirred for 30 min at room temperature the reaction was quenched by the addition of 12 mL of 1M aqueous HCl. The mixture was extracted ethyl acetate (2×40 mL) and the combined organic layers were washed with brine (2×30 mL). The solution was dried over Na$_2$SO$_4$ before being concentrated under reduced pressure. The crude product was used directly in the next reaction without further purification.

MS (EI) m/z 184 (M$^+$), 139 (M−45) base peak.

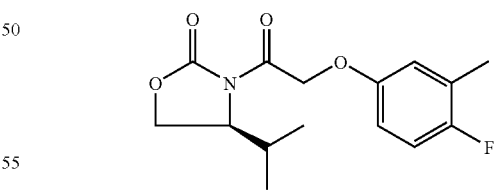

2-(4-Fluoro-3-methylphenoxy)acetyl chloride (C5)

To the crude solution of 2-(4-Fluoro-3-methylphenoxy) acetic acid isolated above in 30 mL DCM was added Oxalyl chloride (776 mg, 6.1 mmol) at 25° C. followed by three drops DMF. After being stirred for 3 h at 25° C., the solvent was evaporated under reduced pressure and the product directly in the next reaction without further purification.

MS (EI) m/z 202 (M$^+$), 139 (M−63) base peak.

(S)-3-(2-(4-Fluoro-3-methylphenoxy)acetyl)-4-isopropyloxazolidin-2-one (D5)

To the solution of (S)-( )-4-Isopropyl-2-oxazolidinone (992 mg, 5.6 mmol) in anhydrous 30 mL THF at −70° C. was slowly added n-BuLi (3.5 mL, 5.6 mmol, 1.6 M in hexane) over 15 minutes. The reaction mixture was stirred for 30 min at −70° C. and to it was slowly added a solution of 2-(4-fluoro-3-methylphenoxy)acetyl chloride crude solution in 4 mL THF. The resulting mixture was stirred at −70° C. for 2 h and the temperature was slowly raised over a period of 1 h. The mixture was poured into 30 mL saturated NH₄Cl and extracted with ethyl acetate (3×40 mL). The combined organic layers were washed with brine (2×30 mL) and dried over Na₂SO₄. The solvent was removed under reduced pressure and the product isolated by Flash column chromatography eluting with 0% to 50% ethyl acetate/hexane to give 2.2 g of the title compound as a light yellow oil.

MS (EI) m/z 295 (M⁺), 43 (M−252) base peak.

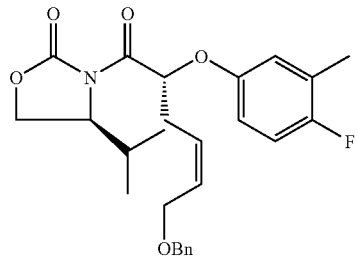

(S)-3-((R,Z)-6-(Benzyloxy)-2-(4-fluoro-3-methylphenoxy)hex-4-enoyl)-4-isopropyloxazolidin-2-one (E5)

To the solution of lithium bis(trimethylsilyl)amide (1.2 mL, 1.2 mmol, 1M in THF) in anhydrous 20 mL THF at −70° C. was slowly added over 15 minutes (S)-3-(2-(4-fluoro-3-methylphenoxy)acetyl)-4-isopropyloxazolidin-2-one (295 mg, 1.0 mmol) as a solution in 3.0 mL THF. The reaction mixture was stirred for 30 min at −70° C. and then was slowly added a pre-cooled solution of (4-Iodo-but-2-enyloxymethyl)-benzene (576 mg, 2.0 mmol) in 3 mL of THF. The resulting mixture was stirred at −70° C. for 1 h and the temperature was slowly raised over a period of 2 h. The mixture was poured into 20 mL saturated NH₄Cl and extracted with ethyl acetate (3×30 mL). The combined organic layers were washed with brine (2×20 mL) and dried over Na₂SO₄. The solvent was removed under reduced pressure and the product isolated by Flash column chromatography eluting with 0% to 50% ethyl acetate/hexane to give 294 mg of the title compound as a light yellow oil.

LC/MS: t_R=11.3 min. MS (API-ES) m/z 278 (M+H⁺+Na⁺).

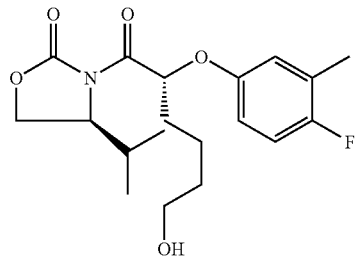

(S)-3-((R)-2-(4-Fluoro-3-methylphenoxy)-6-hydroxyhexanoyl)-4-isopropyloxazolidin-2-one (F5)

(S)-3-((R,Z)-6-(benzyloxy)-2-(4-fluoro-3-methylphenoxy)hex-4-enoyl)-4-isopropyloxazolidin-2-one (250 mg, 0.54 mmol) was dissolved into 5 mL EtOH and to it added 10% Pd/C (250 mg). The solution was saturated with H₂ (stream of H₂ bubbled through solution) and then stirred for 3 h at room temperature under an atmosphere of hydrogen balloon. The mixture was filtered through a bed of Celite and rinsed with ethyl acetate. The solvent was removed under reduced pressure and the crude product used directly in the next step without further purification.

MS (EI) m/z 367 (M⁺), 73 (M−294) base peak.

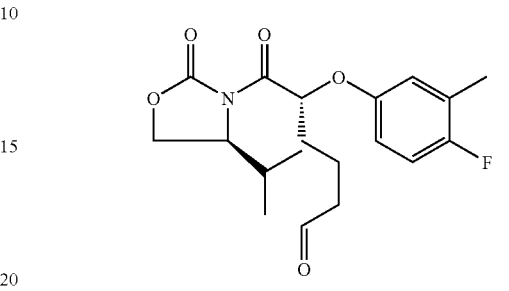

(R)-5-(4-Fluoro-3-methylphenoxy)-6-((S)-4-isopropyl-2-oxooxazolidin-3-yl)-6-oxohexanal (G5)

To the crude solution of (S)-3-((R)-2-(4-fluoro-3-methylphenoxy)-6-hydroxyhexanoyl)-4-isopropyloxazolidin-2-one isolated above (167 mg, 0.45 mmol) in 30 mL DCM was added Dess-Martin periodinane (385 mg, 0.91 mmol) at 25° C. After being stirred for 3 h at 25° C., the mixture was filtered through a bed of Celite and rinsed with more DCM. The solvent was removed under reduced pressure and the product isolated by Flash column chromatography eluting with 0% to 50% ethyl acetate/hexane to give 131 mg of the title compound as a light yellow oil.

MS (EI) m/z 365 (M⁺), 73 (M−292) base peak.

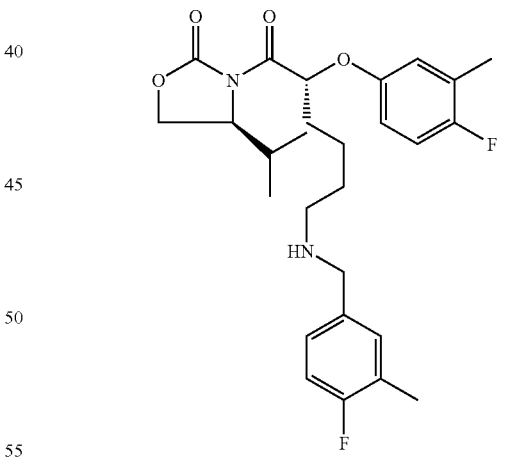

(S)-3-((R)-6-(4-Fluoro-3-methylbenzylamino)-2-(4-fluoro-3-methylphenoxy)hexanoyl)-4-isopropyloxazolidin-2-one (H5)

To a solution of (R)-5-(4-fluoro-3-methylphenoxy)-6-((S)-4-isopropyl-2-oxooxazolidin-3-yl)-6-oxohexanal (70 mg, 0.19 mmol) in 3 mL DCE was added 4-Fluoro-3-methylbenzylamine (32 mg, 0.23 mmol) followed by NaBH(OAc)₃ (56 mg, 0.26 mmol) and AcOH (13.8 mg, 0.23 mmol) at room temperature. The mixture was stirred for 8 h at the room

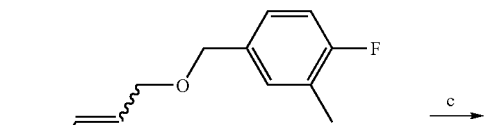

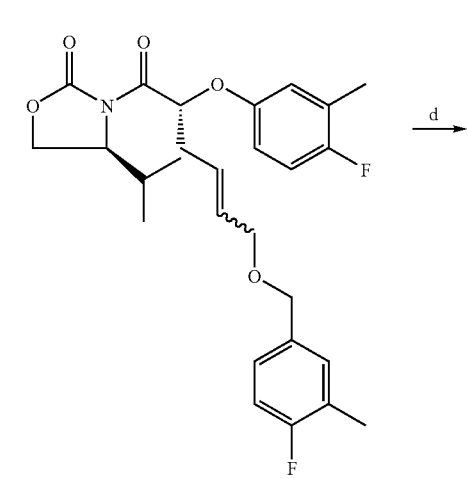

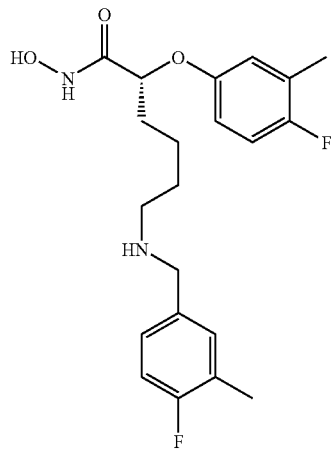

(R)-6-(4-Fluoro-3-methylbenzylamino)-2-(4-fluoro-3-methylphenoxy)-N-hydroxyhexanamide (Compound 168097)

To a crude solution of (S)-3-((R)-6-(4-fluoro-3-methylbenzylamino)-2-(4-fluoro-3-methylphenoxy)hexanoyl)-4-isopropyloxazolidin-2-one isolated above and dissolved in 2 mL of THF, methanol, and 50 wt % NH$_2$OH in H$_2$O (2:2:1) was added KCN (4.0 mg, 0.06 mmol). The resulting mixture stirred for 3 days at room temperature. Evaporation of solvent left the crude from which the product was isolated RP-HPLC eluting with 80% to 2% CH$_3$CN/H$_2$O with 0.025% TFA to give the title compound, 52 mg, as colorless oil.

1H NMR (CD$_3$OD): δ 7.35 (d, 1H, J=7.9), 7.30 (m, 1H), 7.12 (t, 1H, J=8.8), 6.94 (t, 1H, J=9.1), 6.82 (dd, 1H, J=2.6 and 5.9), 6.76 (dd, 1H, J=3.2 and 8.9), 4.53 (t, 1H, J=6.2), 4.13 (s, 2H), 3.03 (t, 2H, J=6.7), 2.30 (s, 3H), 2.20 (s, 3H), 1.94 (m, 2H), 1.74 (m, 2H), 1.58 (m, 2H).

LC/MS: t$_R$=4.7 min. MS (API-ES) m/z 393 (M+H$^+$)

Specific Scheme 6

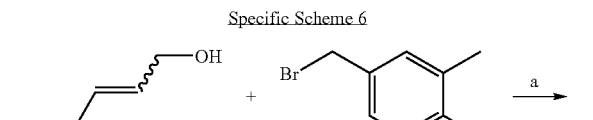

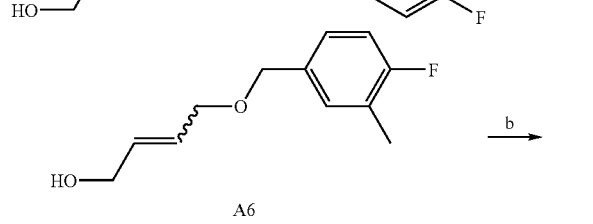

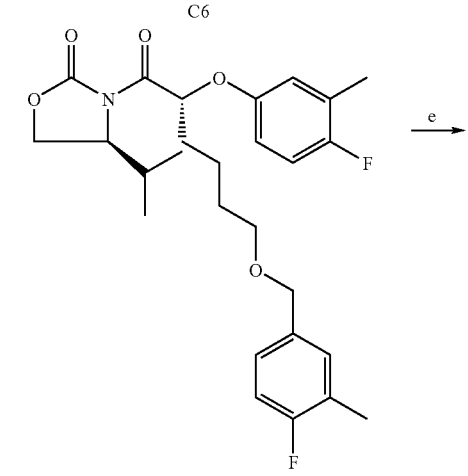

Reagents and conditions: a)) NaH, THF, 25° C., 8 h; b) Ph₃P, Im, I₂, DCM, 0 to 25° C., 3 h; c) (S)-3-(2-(4-fluoro-3-methylphenoxy)acetyl)-4-isopropyloxazolidin-2-one, LiHMDS, THF, −70° C. to RT, 3 h; d) Wilkinson's catalyst, H₂, benzene, 25° C., 12 h; e) NH₂—OH, KCN, H₂O, MeOH, THF, 25° C., 3 days.

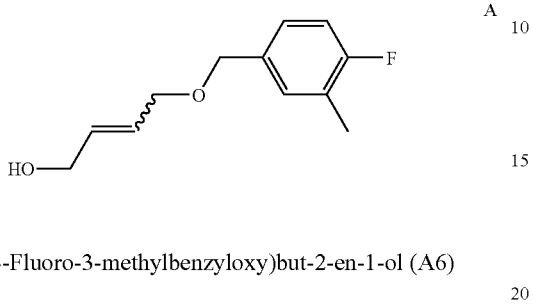

A 4-(4-Fluoro-3-methylbenzyloxy)but-2-en-1-ol (A6)

To a suspension of NaH (1.0 g, 60% oil dispersion) in 80 mL THF was slowly added but-2-ene-1,4-diol (2.0 g, 22 mmol) as a solution in 5 mL THF at room temperature. To this mixture was added dropwise 4-bromomethyl-1-fluoro-2-methyl-benzene (5.0 g, 24 mmol) and the resulting stirred for 8 h at room temperature. The reaction was quenched by the slow addition of 50 mL of saturated NH₄Cl and the mixture extracted with ethyl acetate (3×80 mL). The combined organic layers were washed with brine (2×60 mL) and dried over sodium sulfate. The solvent was removed under reduced pressure and the product isolated by Flash column chromatography eluting with 0% to 50% ethyl acetate/hexane to give 2.3 g of the title compound as a light yellow oil.

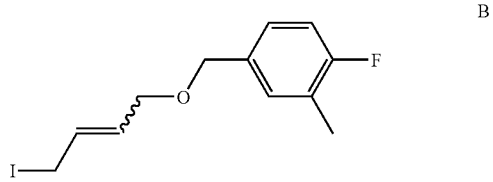

B

1-Fluoro-4-((4-iodobut-2-enyloxy)methyl)-2-methylbenzene (B6)

To a solution of triphenylphosphine (2.6 g, 9.9 mmol) in anhydrous 40 mL DCM was added imidazole (1.4 mg, 20.4 mmol) and iodine (2.5 mg, 9.9 mmol) at 0° C. The reaction mixture was stirred for 30 min at 0° C. and then 4-(4-Fluoro-3-methylbenzyloxy)but-2-en-1-ol (1.3 g, 6.2 mmol) in 10 mL DCM was added to the mixture. The resulting mixture was stirred at 0° C. for 2 h and the temperature was slowly raised to room temp over a period of 2 h. 20 mL of 10% sodium thiosulfate was added and extracted with more DCM (3×30 mL). The combined DCM layer was washed with brine (2×30 mL) and dried over sodium sulfate. Evaporation of solvent left the crude product as an oil from which the product was isolated by Flash column chromatography eluting with 0% to 10% ethyl acetate/hexane to give the title compound, 1.5 g, as a light yellow oil.

MS (EI) m/z 59 (M−261) base peak.

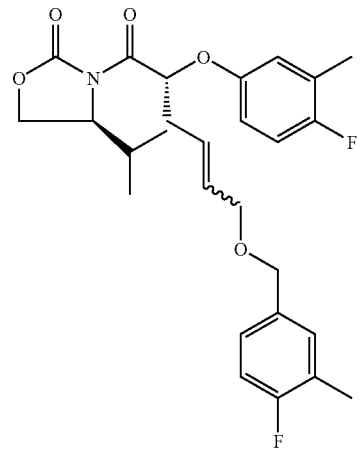

C (S)-3-((R)-6-(4-Fluoro-3-methylbenzyloxy)-2-(4-fluoro-3-methylphenoxy)hex-4-enoyl)-4-isopropyloxazolidin-2-one (C6)

To the solution of lithium bis(trimethylsilyl)amide (1.9 mL, 1.29 mmol, 1M in THF) in anhydrous 30 mL THF at −70° C. was slowly added over 15 minutes (S)-3-(2-(4-fluoro-3-methylphenoxy)acetyl)-4-isopropyloxazolidin-2-one (480 mg, 1.6 mmol) as a solution in 4.0 mL THF. The reaction mixture was stirred for 30 min at −70° C. and then was slowly added a pre-cooled solution of 1-Fluoro-4-((4-iodobut-2-enyloxy)methyl)-2-methylbenzene (1.0 g, 3.2 mmol) in 4 mL of THF. The resulting mixture was stirred at −70° C. for 1 h and the temperature was slowly raised over a period of 2 h. The mixture was poured into 40 mL saturated NH₄Cl and extracted with ethyl acetate (3×40 mL). The combined organic layers were washed with brine (2×30 mL) and dried over Na₂SO₄. The solvent was removed under reduced pressure and the product isolated by Flash column chromatography eluting with 0% to 50% ethyl acetate/hexane to give 430 mg of the title compound as a light yellow oil.

MS (EI) m/z 129 (M−358) base peak.

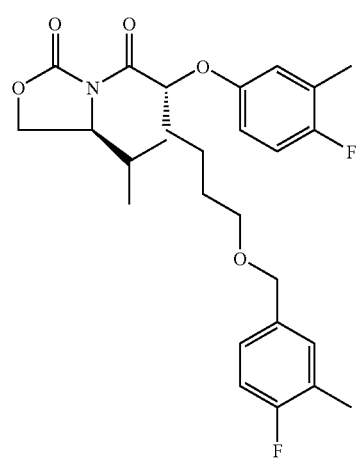

D

(S)-3-((R)-6-(4-Fluoro-3-methylbenzyloxy)-2-(4-fluoro-3-methylphenoxy)hexanoyl)-4-isopropyloxazolidin-2-one (D6)

(S)-3-((R)-6-(4-fluoro-3-methylbenzyloxy)-2-(4-fluoro-3-methylphenoxy)hex-4-enoyl)-4-isopropyloxazolidin-2-one (430 mg, 0.88 mmol) was dissolved into 4 mL benzene and to it added Wilkinson catalysis (81.0 mg, 0.088 mmol). The solution was saturated with $H_2$ (stream of $H_2$ bubbled through solution) and then stirred for 8 h at room temperature under an atmosphere of hydrogen balloon. The solvent was removed under reduced pressure and the product isolated by flash column chromatography eluting with 0% to 30% ethyl acetate/hexane to give 418 mg of the title compound as a colorless oil.

MS (EI) m/z 489 ($M^+$), 123 (M−366) base peak.

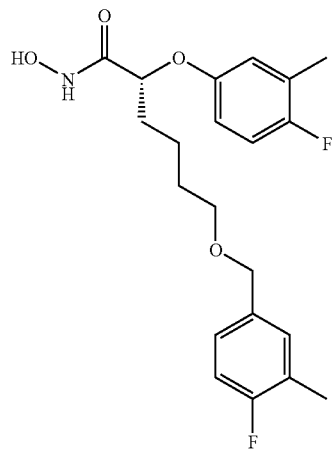

(R)-6-(4-Fluoro-3-methylbenzyloxy)-2-(4-fluoro-3-methylphenoxy)-N-hydroxyhexanamide (Compound 168113)

To a solution of (S)-3-((R)-6-(4-fluoro-3-methylbenzyloxy)-2-(4-fluoro-3-methylphenoxy)hexanoyl)-4-isopropyloxazolidin-2-one (100 mg, 0.20 mmol) dissolved in 2 mL of THF, methanol, and 50 wt % $NH_2OH$ in $H_2O$ (2:2:1) was added KCN (4.0 mg, 0.06 mmol). The resulting mixture stirred for 3 days at room temperature. The reaction was quenched by the addition of 1M aqueous HCl (10 mL) and the resulting mixture extracted with ethyl acetate (3×10 mL). The combined organic layers were washed with brine (2×5 mL). The product was isolated by flash column chromatography eluting with 0% to 10% methanol/DCM to give the title compound (54.2 mg) as colorless oil.

1H NMR ($CD_3OD$): δ 7.19 (d, 1H, J=7.9), 7.13 (m, 1H), 6.93 (m, 2H) 6.79 (dd, 1H, J=5.9 and 6.2), 6.74 (dd, 1H, J=3.5 and 8.9), 4.48 (t, 1H, J=6.2), 4.41 (s, 2H), 3.48 (t, 2H, J=5.9), 2.24 (s, 3H), 2.21 (s, 3H), 1.90 (m, 2H), 1.62 (m, 4H).

LC/MS: $t_R$=8.9 min. MS (API-ES) m/z 394 ($M+H^+$)

Specific Scheme 7

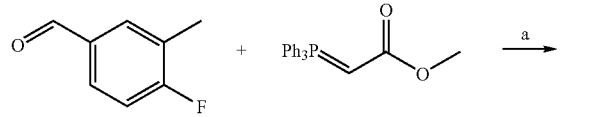

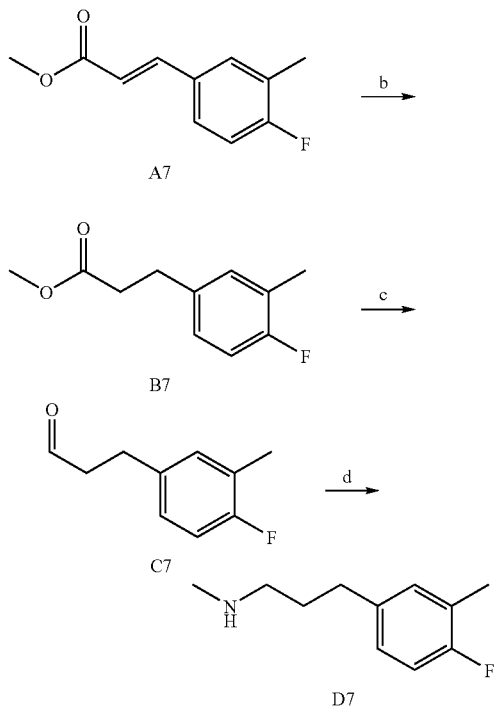

Reagents and conditions: a) THF, 25° C., 8 h; b) 10% Pd/C, $H_2$, MeOH, 25° C., 3 h; c) DIBAL-H, DCM, −70° C., 30 min; d) $MeNH_2 \cdot HCl$, $NaBH(OAc)_3$, DCE, 25° C., 8 h.

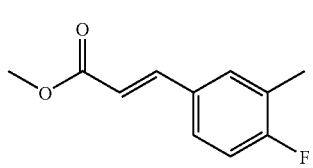

(E)-Methyl 3-(4-fluoro-3-methylphenyl)acrylate (A7)

To a suspension of (triphenyl-15-phosphanylidene)-acetic acid methyl ester (3.6 g, 10.8 mmol) in 50 mL anhydrous THF at 25° C. was added 4-Fluoro-3-methyl-benzaldehyde (1.0 g, 7.2 mmol) in 10 mL THF. The reaction mixture was stirred for 8 h at 25° C. The solvent was removed under reduced pressure and the product isolated by flash column chromatography eluting with 0% to 20% ethyl acetate/hexane to give 1.3 g of the title compound as a white solid.

MS (EI) m/z 194 ($M^+$), 163 (M−31) base peak.

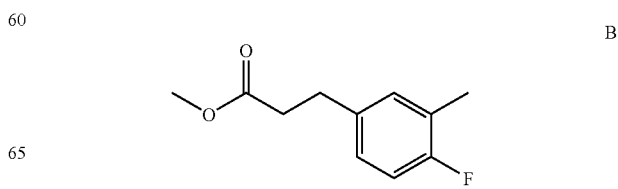

Methyl 3-(4-fluoro-3-methylphenyl)propanoate (B7)

(E)-Methyl 3-(4-fluoro-3-methylphenyl)acrylate (1.3 g, 6.7 mmol) was dissolved into 58 mL MeOH and to it added 10% Pd/C (750 mg). The solution was saturated with $H_2$ and then stirred for 3 h at room temperature under an atmosphere of hydrogen balloon. The mixture was filtered through a bed of Celite and rinsed with ethyl acetate. The solvent was removed under reduced pressure and the crude product used directly in the next step without further purification.

MS (EI) m/z 196 (M$^+$), 136 (M−60) base peak.

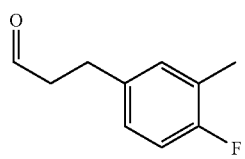

3-(4-Fluoro-3-methylphenyl)propanal (C7)

To the solution of methyl 3-(4-fluoro-3-methylphenyl)propanoate isolated above in anhydrous 50 mL DCM at −70° C. was slowly added DIBAL-H (21 mL, 21 mmol, 1 M in cyclohexane). The reaction mixture was stirred for 30 min at −70° C. The excess reagents were destroyed by dropwise addition of 40 mL 4% aqueous $H_2SO_4$. The mixture was and extracted with ethyl acetate (3×30 mL) and the combined organic layers washed with brine (2×20 mL) and dried over sodium sulfate. The solvent was removed under reduced pressure and the product isolated by flash column chromatography eluting with 0% to 50% ethyl acetate/hexane to give 1.1 g of the title compound as a colorless oil.

MS (EI) m/z 166 (M$^+$), 123 (M−43) base peak.

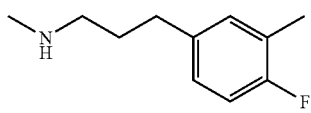

3-(4-Fluoro-3-methylphenyl)-N-methylpropan-1-amine (D7)

To a solution of 3-(4-fluoro-3-methylphenyl)propanal (1.0 g, 6 mmol) in 20 mL MeOH was added MeNH$_2$HCl (556 mg, 7.2 mmol) followed by NaBH$_3$CN (452 mg, 7.2 mmol) at room temperature. The mixture was stirred for 2 h at the room temperature. The reaction was quenched by pouring into 20 mL 5% aqueous NaOH and diluted with ethyl acetate. The mixture was extracted with more ethyl acetate (3×15 mL) and the combined organic layers washed with brine (2×10 mL) and dried over Na$_2$SO$_4$. The mixture was concentrated under reduced pressure and the product isolated by flash column chromatography eluting with 0% to 10% MeOH/DCM to provide 461 mg of the title compound as an colorless oil.

MS (EI) m/z 181 (M$^+$), 44 (M−137) base peak.

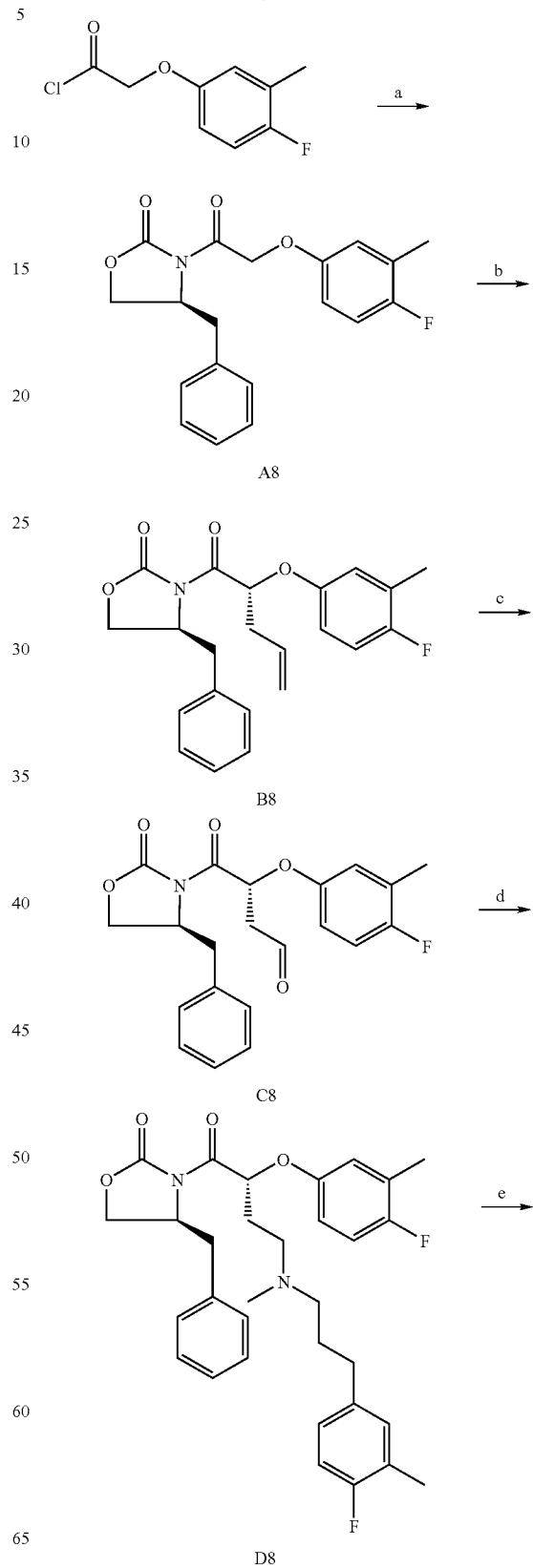

Specific Scheme 8

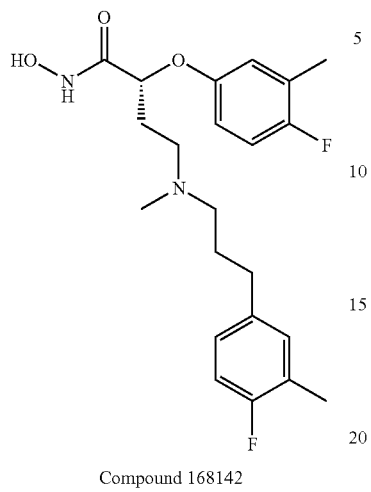

Compound 168142

Reagents and conditions: a) (S)-4-Benzyl-2-oxazolidione, n-BuLi, THF, −70° C. to RT, 3 h; b) allyl iodide, LiHMDS, THF, −70° C. to RT, 3 h; c) O$_3$, Ph$_3$P, DCM, −70° C. to RT, 4 h; d) 3-(4-Fluoro-3-methylphenyl)-N-methylpropan-1-amine, NaBH(OAc)$_3$, DCE, 25° C., 8 h; e) NH$_2$—OH, KCN, H$_2$O, MeOH, THF, 25° C., 3 days.

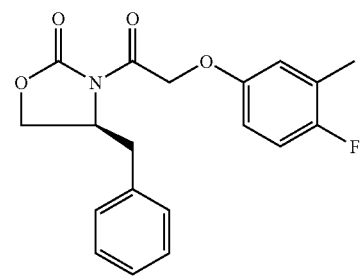

(S)-4-Benzyl-3-(2-(4-fluoro-3-methylphenoxy)acetyl)oxazolidin-2-one (A8)

To the solution of (S)-4-Benzyl-2-oxazolidinone (857 mg, 4.8 mmol) in anhydrous 30 mL THF at −70° C. was slowly added n-BuLi (3.0 mL, 4.8 mmol, 1.6 M in hexane) over 15 minutes. The reaction mixture was stirred for 30 min at −70° C. and to it was slowly added a solution of 2-(4-fluoro-3-methylphenoxy)acetyl chloride crude solution in 4 mL THF. The resulting mixture was stirred at −70° C. for 2 h and the temperature was slowly raised over a period of 1 h. The mixture was poured into 30 mL saturated NH$_4$Cl and extracted with ethyl acetate (3×40 mL). The combined organic layers were washed with brine (2×30 mL) and dried over Na$_2$SO$_4$. The solvent was removed under reduced pressure and the product isolated by Flash column chromatography eluting with 0% to 50% ethyl acetate/hexane to give 1.5 g of the title compound as a light yellow oil.

MS (EI) m/z 343 (M$^+$), 117 (M−226) base peak.

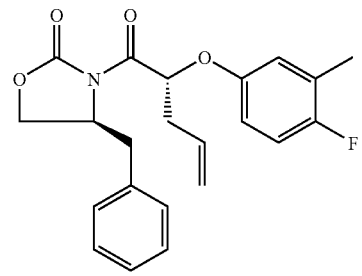

(S)-4-benzyl-3-((R)-2-(4-fluoro-3-methylphenoxy)pent-4-enoyl)oxazolidin-2-one (B8)

To the solution of lithium bis(trimethylsilyl)amide (5.2 mL, 5.2 mmol, 1M in THF) in anhydrous 30 mL THF at −70° C. was slowly added over 15 minutes (S)-4-Benzyl-3-(2-(4-fluoro-3-methylphenoxy)acetyl)oxazolidin-2-one (1.5 g, 4.3 mmol) as a solution in 8.0 mL THF. The reaction mixture was stirred for 30 min at −70° C. and then was slowly added a pre-cooled solution of allyl iodide (2.2 g, 13 mmol) in 8 mL of THF. The resulting mixture was stirred at −70° C. for 1 h and the temperature was slowly raised over a period of 2 h. The mixture was poured into 60 mL saturated NH$_4$Cl and extracted with ethyl acetate (3×40 mL). The combined organic layers were washed with brine (2×30 mL) and dried over Na$_2$SO$_4$. The solvent was removed under reduced pressure and the product isolated by Flash column chromatography eluting with 0% to 50% ethyl acetate/hexane to give 521 mg of the title compound as a light yellow oil.

MS (EI) m/z 383 (M$^+$), 91 (M−292) base peak.

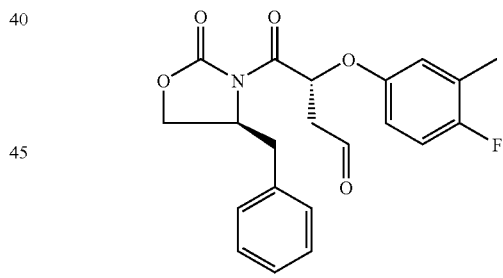

(R)-4-((S)-4-benzyl-2-oxooxazolidin-3-yl)-3-(4-fluoro-3-methylphenoxy)-4-oxobutanal (C8)

A solution of (S)-4-benzyl-3-((R)-2-(4-fluoro-3-methylphenoxy)pent-4-enoyl)oxazolidin-2-one (300 mg, 0.78 mmol) in 20 mL DCM was cooled to −70° C. and O$_3$ bubbled through it until the solution showed a faint blue color. The solution was purged of any remaining O$_3$ tubing by sparging with N$_2$ for about 30 minutes. Triphenyl-phosphine (820 mg, 3.1 mmol) was added at −70° C. and the temperature was slowly raised to room temperature. The resulting mixture was stirred for 3 h. After concentrating under reduced pressure, the product was isolated by silica gel chromatography to afford the title compound 125 mg, as an colorless oil.

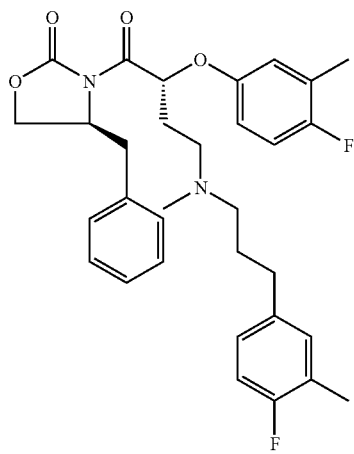

(S)-4-benzyl-3-((R)-2-(4-fluoro-3-methylphenoxy)-4-((3-(4-fluoro-3-methylphenyl)propyl)(methyl)amino)butanoyl)oxazolidin-2-one (D8)

To a solution of (R)-4-((S)-4-benzyl-2-oxooxazolidin-3-yl)-3-(4-fluoro-3-methylphenoxy)-4-oxobutanal (35 mg, 0.091 mmol) in 3 mL DCE was added 3-(4-Fluoro-3-methylphenyl)-N-methylpropan-1-amine (22 mg, 0.12 mmol) followed by NaBH(OAc)$_3$ (29.5 mg, 0.14 mmol) and AcOH (7.2 mg, 0.12 mmol) at room temperature. The mixture was stirred for 8 h at the room temperature. The reaction was quenched by pouring into 10 mL 5% aqueous NaOH and diluted with ethyl acetate. The mixture was extracted with more ethyl acetate (3×15 mL) and the combined organic layers washed with brine (2×10 mL) and dried over Na$_2$SO$_4$. The solvent was removed under reduced pressure and the crude product used directly in the next step without further purification.

LC/MS: $t_R$=6.2 min. MS (API-ES) m/z 425 (M+H$^+$−125)

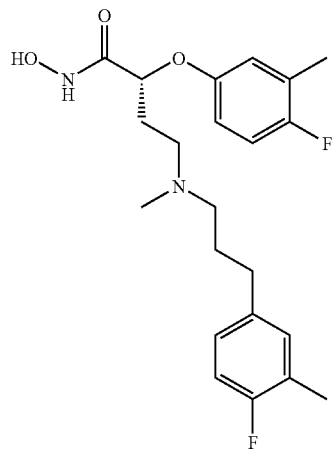

(R)-2-(4-fluoro-3-methylphenoxy)-4-((3-(4-fluoro-3-methylphenyl)propyl)(methyl)amino)-N-hydroxybutanamide (Compound 168142)

To a crude solution of (S)-4-benzyl-3-((R)-2-(4-fluoro-3-methylphenoxy)-4-((3-(4-fluoro-3-methylphenyl)propyl)(methyl)amino)butanoyl)oxazolidin-2-one isolated above and dissolved in 2 mL of THF, methanol, and 50 wt % NH$_2$OH in H$_2$O (2:2:1) was added KCN (4.0 mg, 0.06 mmol). The resulting mixture stirred for 3 days at room temperature. Evaporation of solvent left the crude from which the product was isolated RP-HPLC eluting with 80% to 2% CH$_3$CN/H$_2$O with 0.025% TFA to give the title compound, 3.1 mg, as colorless oil.

1H NMR (CD$_3$OD): δ 7.10 (d, 1H, J=6.74), 7.03 (m, 1H), 6.96 (d, 1H, J=9.37), 6.91-6.70 (m, 3H), 4.71 (t, 1H, J=5.56), 3.30 (m, 4H), 2.86 (s, 3H), 2.65 (t, 2H, J=5.86), 2.22 (br, 6H), 2.01 (m, 4H).

LC/MS: $t_R$=5.4 min. MS (API-ES) m/z 407 (M+H$^+$)

Specific Scheme 9

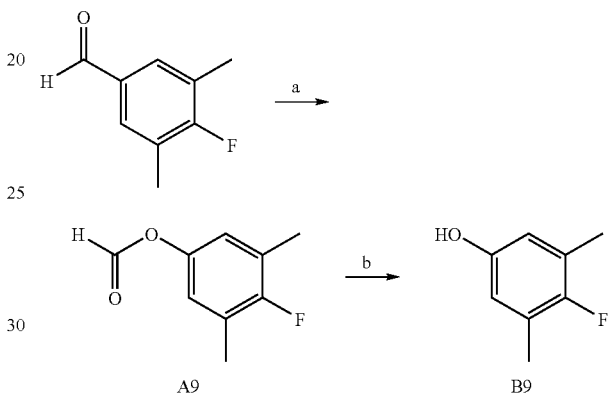

Reagents and conditions: a) mCPBA, DCM, 25° C., 20 h; b) 5% KOH (aq), dioxane, 25° C., 30 min.

Formic Acid 4-fluoro-3,5-dimethyl-phenyl ester (A9)

To a solution of 4-fluoro-3,5-dimethyl-benzaldehyde (1.0 g, 6.4 mmol) in 20 mL DCM was added mCPBA (1.2 g, 7.6 mmol) at 25° C. After being stirred for 20 h at 25° C., the reaction was quenched by the addition of 40 mL of 5% aqueous potassium carbonate. The mixture was extracted DCM (3×30 mL) and the combined DCM layer was washed with brine (2×30 mL). The solution was dried over Na$_2$SO$_4$ before being concentrated under reduced pressure. The crude product was used directly in the next reaction without further purification.

MS (EI) m/z 168 (M$^+$), 125 (M−43) base peak.

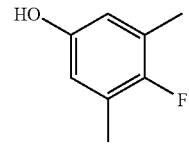

4-Fluoro-3,5-dimethyl-phenol (B9)

To a solution of acetic acid 4-fluoro-3,5-dimethyl-phenyl ester in 10 mL dioxane was added 10 mL aqueous 5% KOH at 25° C. After being stirred for 30 min at 25° C., the reaction was quenched by the addition of 12 mL of 1M aqueous HCl. The mixture was extracted ethyl acetate (3×30 mL) and the combined organic layers were washed with brine (2×30 mL). The solution was dried over $Na_2SO_4$ before being concentrated under reduced pressure. The product was isolated by silica gel chromatography to afford the title compound 987 mg, as a light yellow oil.

MS (EI) m/z 140 (M$^+$), 140 (M) base peak.

Abbreviations:

DMF=dimethylformamide

HOBt=1-hydroxybenzotriazole

NMM=N-methylmorpholine

EDC=N-(-dimethylaminopropyl)-N'-ethylcarbodiimide

DCM=dichloromethane

DCE=1,2-dichloroethane

TFA=trifluoroacetic acid

MS=molecular sieves

LiHMDS=lithium bis(trimethylsilyl)amide

DIBAL-H=diisobutylaluminum hydride

TABLE 1

| Compounds |
|---|
| ![structure] |

2-(4-Fluoro-3-methyl-phenoxy)-N-hydroxy-acetamide (Compound 167182) Prepared according to General Scheme 1.
LC-MS: $t_R$ = 4.4 min, m/z 200 (M + H)$^+$

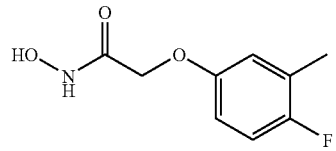

2-(4-Fluoro-3-methyl-phenoxy)-hexanoic acid hydroxyamide (Compound 167163) Prepared according to General Scheme 1.
LC-MS: $t_R$ = 6.9 min, m/z 256 (M + H)$^+$

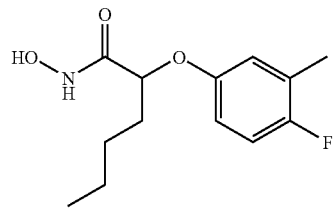

2-(4-Fluoro-3-methyl-phenylsulfanyl)-hexanoic acid hydroxyamide (Compound 167303) Prepared according to General Scheme 2.
LC-MS: $t_R$ = 7.2 min, m/z 272 (M + H)$^+$

TABLE 1-continued

| Compounds |
|---|

2-(4-Fluoro-3-methyl-benzenesulfinyl)-hexanoic acid hydroxyamide (Compound 167316) Prepared according to General Scheme 4.
LC-MS: $t_R$ = 4.7 and 5.3 min, m/z 288 (M + H)$^+$ syn-2-(4-Fluoro-3-methyl-benzenesulfinyl)-hexanoic acid hydroxyamide (Compound 167351) Prepared according to General Scheme 4.
LC-MS: $t_R$ = 4.7 min, m/z 288 (M + H)$^+$ anti-2-(4-Fluoro-3-methyl-benzenesulfinyl)-hexanoic acid hydroxyamide (Compound 167352) Prepared according to General Scheme 4.
LC-MS: $t_R$ = 5.3 min, m/z 288 (M + H)$^+$ 2-(4-Fluoro-3-methyl-benzenesulfonyl)-hexanoic acid hydroxyamide (Compound 167304) Prepared according to General Scheme 3.
LC-MS: $t_R$ = 6.0 min, m/z 304 (M + H)$^+$

TABLE 2

| Compounds |
|---|
| 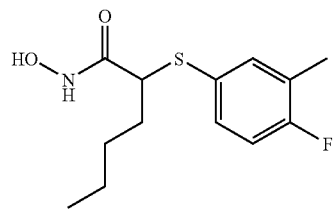 |

(R)-2-(4-Fluoro-3-methyl-phenoxy)-pentanoic acid hydroxyamide (Compound 168090) Prepared according to General Scheme 5.

TABLE 2-continued

Compounds

¹H-NMR (CD₃OD):. δ 6.91 (t, 1H, J = 9.0), 6.80 (dd, 1H, J = 2.7 and 6.3), 6.73 (m, 1H), 4.46 (t, 1H, J = 5.6), 2.21 (d, 3H, J = 2.0), 1.85 (m, 2H), 1.51 (m, 2H), 0.96 (t, 3H, J = 7.4). LC/MS: $t_R$ = 6.3 min. MS (API-ES) m/z 242 (M + H⁺)

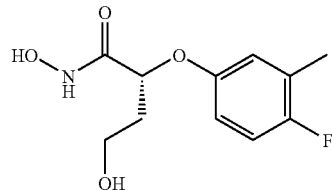

(R)-2-(4-fluoro-3-methylphenoxy)-N,4-dihydroxybutanamide (Compound 168093) Prepared according to General Scheme 7.
¹H-NMR (CD₃OD):. δ 6.92 (t, 1H, J = 9.1), 6.82 (m, 1H), 6.75 (m, 1H), 4.66 (t, 1H, J = 6.2), 3.73 (t, 2H, J = 6.7), 2.22 (s, 3H), 2.07 (m, 2H). LC/MS: $t_R$ = 3.6 min. MS (API-ES) m/z 244 (M + H⁺)

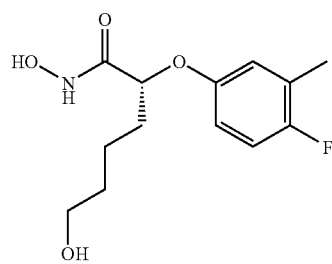

(R)-2-(4-fluoro-3-methylphenoxy)-N,6-dihydroxyhexanamide (Compound 168176) Prepared according to General Scheme 5
LC/MS: $t_R$ = 4.6 min. MS (API-ES) m/z 272 (M + H⁺)

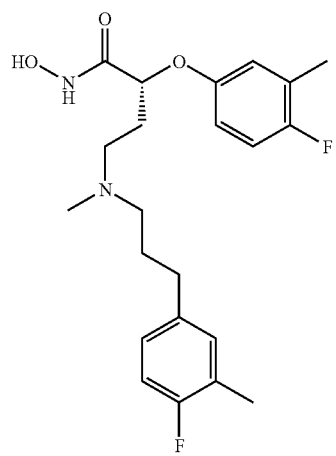

(R)-2-(4-fluoro-3-methylphenoxy)-4-((3-(4-fluoro-3-methylphenyl)propyl)(methyl)amino)-N-hydroxybutanamide (Compound 168142) Prepared according to General Scheme 5.
¹H-NMR (CD₃OD):. δ 7.10 (d, 1H, J = 6.74), 7.03 (m, 1H), 6.96 (d, 1H, J = 9.37), 6.91-6.70 (m, 3H), 4.71 (t, 1H, J = 5.56), 3.30 (m, 4H), 2.86 (s, 3H), 2.65 (t, 2H, J = 5.86), 2.22 (br, 6H), 2.01 (m, 4H). LC/MS: $t_R$ = 5.4 min. MS (API-ES) m/z 407 (M + H⁺)

TABLE 2-continued

Compounds (R)-2-(4-fluoro-3-methylphenoxy)-N-hydroxy-4-((S)-3-(piperidin-1-ylmethyl)piperidin-1-yl)butanamide (COMPOUND 168143) Prepared according to General Scheme 7.
LC/MS: $t_R$ = 1.2 min. MS (API-ES) m/z 408 (M + H⁺)

(R)-6-(4-fluoro-3-methylbenzylamino)-2-(4-fluoro-3-methylphenoxy)-N-hydroxyhexanamide (Compound 168097) Prepared according to General Scheme 5.
¹H-NMR (CD₃OD):. δ 7.35 (d, 1H, J = 7.9), 7.30 (m, 1H), 7.12 (t, 1H, J = 8.8), 6.94 (t, 1H, J = 9.1), 6.82 (dd, 1H, J = 2.6 and 5.9), 6.76 (dd, 1H, J = 3.2 and 8.9), 4.53 (t, 1H, J = 6.2), 4.13 (s, 2H), 3.03 (t, 2H, J = 6.7), 2.30 (s, 3H), 2.20 (s, 3H), 1.94 (m, 2H), 1.74 (m, 2H), 1.58 (m, 2H). LC LC/MS: $t_R$ = 4.7 min. MS (API-ES) m/z 393 (M + H⁺)

(R)-2-(4-fluoro-3,5-dimethylphenoxy)-6-(4-fluoro-3-methylbenzylamino)-N-hydroxyhexanamide (COMPOUND 168100) Prepared according to

TABLE 2-continued

Compounds

General Scheme 5.
$^1$H-NMR (CD$_3$OD):. δ 7.34 (d, 1H, J = 5.5), 7.30 (m, 1H), 7.11 (t, 1H, J = 9.1), 6.61 (d, 2H, J = 5.8), 4.50 (t, 1H, J = 5.7), 4.13 (s, 2H), 3.02 (t, 2H, J = 8.0), 2.30 (s, 3H), 2.19 (d, 6H, J = 1.8), 1.94 (q, 2H, J = 6.9 and 15.2), 1.74 (m, 2H), 1.58 (m, 2H). LC LC/MS: t$_R$ = 5.1 min. MS (API-ES) m/z 407 (M + H$^+$)

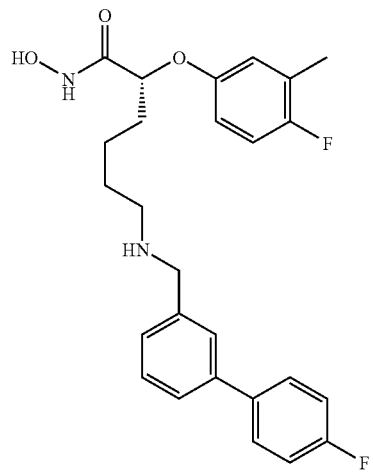

(R)-2-(4-fluoro-3-methylphenoxy)-6-((4'-fluorobiphenyl-3-yl)methylamino)-N-hydroxyhexanamide (Compound 168178) Prepared according to General Scheme 5
$^1$H-NMR (CD$_3$OD): δ 7.73-7.64 (m, 4H), 7.54 (t, 1H, J = 7.6), 7.45 (dd, 1H, J = 1.1 and 7.4), 7.19 (t, 2H, J = 8.8), 6.91 (t, 1H, J = 9.1), 6.81 (dd, 1H, J = 3.1 and 5.7), 6.74 (dd, 1H, J = 4.1 and 8.3), 4.53 (t, 1H, J = 6.0), 4.26 (s, 2H), 3.08 (t, 2H, J = 7.8), 2.21 (s, 3H), 1.94 (m, 2H), 1.74 (m, 2H), 1.60 (m, 2H). LC/MS: t$_R$ = 5.8 min. MS (API-ES) m/z 454 (M + H$^+$)

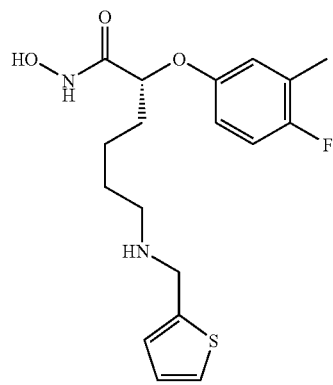

(R)-2-(4-fluoro-3-methylphenoxy)-N-hydroxy-6-(thiophen-2-ylmethylamino)hexanamide (Compound 168177) Prepared according to General Scheme 5
$^1$H-NMR (CD$_3$OD):. δ 7.57 (dd, 1H, J = 1.2 and 5.2), 7.28 (d, 1H, J = 3.2), 7.12 (t, 1H, J = 4.3), 6.94 (t, 1H, J = 9.1), 6.82 (dd, 1H, J = 3.0 and 5.9), 6.75 (dd, 1H, J = 3.5 and 8.7), 4.53 (t, 1H, J = 5.8), 4.43 (s, 2H), 3.04 (t, 2H, J = 8.0), 2.22 (s, 3H), 1.94 (m, 2H), 1.74 (m, 2H), 1.59 (m, 2H). LC/MS: t$_R$ = 4.0 min. MS (API-ES) m/z 367 (M + H$^+$)

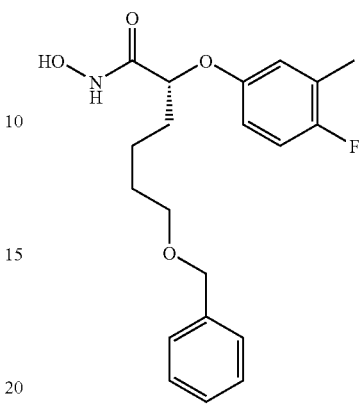

(R)-6-(4-fluoro-3-methylbenzyloxy)-2-(4-fluoro-3-methylphenoxy)-N-hydroxyhexanamide (COMPOUND 168101) Prepared according to General Scheme 6.
$^1$H-NMR (CD$_3$OD):. δ 7.31 (s, 5H), 6.92 (t, 1H, J = 9.1), 6.82 (m, 1H), 6.75 (m, 1H), 4.47 (m, 3H), 3.49 (t, 2H, J = 5.9), 2.20 (s, 3H), 1.90 (m, 2H), 1.63 (m, 4H). LC LC/MS: t$_R$ = 8.2 min. MS (API-ES) m/z 362 (M + H$^+$)

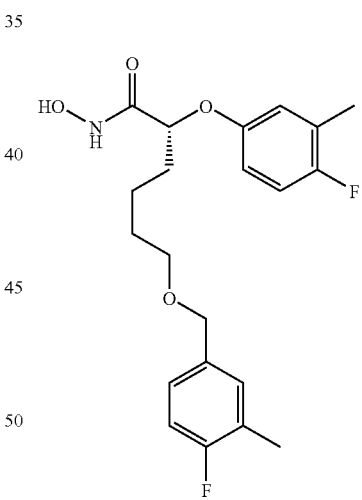

(R)-6-(4-fluoro-3-methylbenzyloxy)-2-(4-fluoro-3-methylphenoxy)-N-hydroxyhexanamide (COMPOUND 168113) Prepared according to General Scheme 6.
$^1$H-NMR: (CD$_3$OD):. δ 7.19 (d, 1H, J = 7.9), 7.13 (m, 1H), 6.93 (m, 2H) 6.79 (dd, 1H, J = 5.9 and 6.2), 6.74 (dd, 1H, J = 3.5 and 8.9), 4.48 (t, 1H, J = 6.2), 4.41 (s, 2H), 3.48 (t, 2H, J = 5.9), 2.24 (s, 3H), 2.21 (s, 3H), 1.90 (m, 2H), 1.62 (m, 4H). LC LC/MS: t$_R$ = 8.8 min. MS (API-ES) m/z 394 (M + H$^+$)

TABLE 2-continued

Compounds

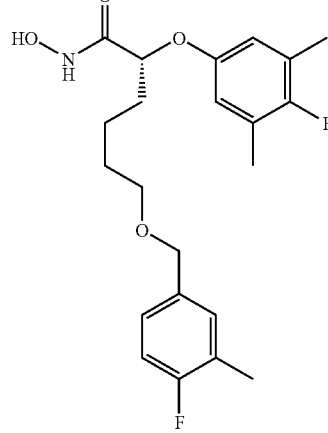

(R)-2-(4-fluoro-3,5-dimethylphenoxy)-6-(4-fluoro-3-methylbenzyloxy)-N-hydroxyhexanamide (Compound 167135) Prepared according to General Scheme 6.
$^1$H-NMR (CD$_3$OD):. δ 7.65 (m, 1H), 7.18 (d, 1H, J = 1.2), 6.95 (t, 1H, J = 8.8), 6.61 (d, 2H, J = 5.8), 4.45 (t, 1H, J = 6.2), 4.40 (s, 2H), 3.47 (t, 2H, J = 6.1), 2.24 (s, 3H), 2.18 (d, 6H, J = 1.9), 1.89 (m, 2H), 1.62 (m, 4H). LC/MS: $t_R$ = 9.4 min. MS (API-ES) m/z 408 (M + H$^+$)

TABLE 3

Compounds 2-(4-fluorophenoxy)-N-hydroxyacetamide (Compound 168128) Prepared according to General Scheme 1.
$^1$H-NMR (CD$_3$OD):. δ 7.00 (m, 4H), 4.52 (s, 2H). LC/MS: $t_R$ = 3.2 min. MS (API-ES) m/z 186 (M + H$^+$)

2-(4-chlorophenoxy)-N-hydroxyacetamide (Compound 168129) Prepared according to General Scheme 1.
$^1$H-NMR (CD$_3$OD):. δ 7.27 (d, 2H, J = 9.0), 6.97 (d, 2H, J = 9.0), 4.54 (s, 2H). LC/MS: $t_R$ = 4.5 min. MS (API-ES) m/z 202 (M + H$^+$)

2-(3,4-difluorophenoxy)-N-hydroxyacetamide (Compound 168130) Prepared according to General Scheme 1.
$^1$H-NMR (CD$_3$OD):. δ 7.19 (q, 1H, J = 9.3 and 19.4), 6.96 (m, 1H), 6.79 (m, 1H), 4.53 (s, 2H). LC/MS: $t_R$ = 4.0 min. MS (API-ES) m/z 204 (M + H$^+$)

TABLE 3-continued

Compounds 2-(3-chloro-4-fluorophenoxy)-N-hydroxyacetamide (Compound 167127) Prepared according to General Scheme 1.
$^1$H-NMR (CD$_3$OD):. δ 7.20-711 (m, 2H), 6.95 (m, 1H), 4.54 (d, 2H, J = 1.4). LC/MS: $t_R$ = 4.8 min. MS (API-ES) m/z 220 (M + H$^+$)

2-(4-Fluoro-3,5-dimethyl-phenoxy)-N-hydroxy-acetamide (Compound 168115) Prepared according to General Scheme 1.
$^1$H-NMR (CD$_3$OD):. δ 6.65 (d, 2H, J = 5.5), 4.47 (s, 2H), 2.21 (d, 6H, J = 2.0). LC/MS: $t_R$ = 5.4 min. MS (API-ES) m/z 214 (M + H$^+$)

TABLE 4

Compounds (R,Z)-6-(benzyloxy)-2-(3-chloro-4-fluorophenoxy)-N-hydroxyhex-4-enamide (Compound 168160) Prepared according to General Scheme 6.
LC/MS: $t_R$ = 8.1 min. MS (API-ES) m/z 380 (M + H$^+$)

R)-6-(benzyloxy)-2-(3-chloro-4-fluorophenoxy)-N-hydroxyhexanamide (Compound 168187) Prepared according to General Scheme 6

TABLE 4-continued

Compounds $^1$H-NMR (CD$_3$OD): δ 7.31 (m, 5H), 7.14 (t, 2H, J = 9.0), 7.07 (m, 1H), 6.90 (m, 1H), 4.54 (t, 1H, J = 5.8), 4.48 (s, 2H), 3.50 (t, 2H, J = 5.7), 1.92 (m, 2H), 1.70-1.51 (m, 4H). LC/MS: t$_R$ = 1.07 min. MS (API-ES) m/z 382 (M + H$^+$)

What is claimed is:

1. A compound of the formula

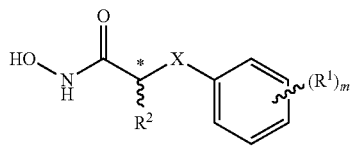

where
R$^1$ is F, Cl, Br, I, alkyl of 1-3 carbons, alkoxy of 1-3 carbons, thioalkoxy of 1-3 carbons, phenyl, O-phenyl, CN, CF$_3$, OCF$_3$, OH, NH$_2$, NHC$_1$-C$_6$alkyl, N(C$_1$-C$_6$alkyl)$_2$, COOH or COO(C$_1$-C$_6$alkyl);

m is an integer having the value of 1 to 3;

R$^2$ is alkyl of 2-6 carbons; C$_1$-C$_6$ alkylphenyl where phenyl is substituted with 0-3 R$^1$ groups, C$_2$-C$_6$alkenylO(CH$_2$)$_n$phenyl where alkenyl has 2 to 6 carbons and one double bond and phenyl is substituted with 0-3 R$^1$ groups, C$_1$-C$_6$ alkylcyclohexyl, (CH$_2$)$_n$OR$^3$, (CH$_2$)$_n$NHR$^4$, NR$^4$C$_1$-C$_6$alkyl, (CH$_2$)$_n$CF$_3$, CH$_2$OCH$_2$-phenyl; (CH$_2$)$_n$NH(CH$_2$)$_n$R$^4$, (CH$_2$)$_n$NR$^6$R$^4$, (CH$_2$)$_n$NR$^6$(CH$_2$)$_n$R$^4$, (CH$_2$)$_n$O (CH$_2$)$_n$R$^4$, (CH$_2$)$_n$OR$^4$, n is an integer having the value of 1 to 8;

R$^3$ is H, alkyl of 1 to 6 carbons, alkylphenyl where the alkylgroup has 1 to 6 carbons and the phenyl is substituted with 0-3 R$^1$ groups;

R$^4$ is H, cyclohexyl, C(O)alkyl of 1 to 4 carbons, C(O) alkylphenyl where the alkylgroup has 1 to 4 carbons and the phenyl is substituted with 0-3 R$^1$ groups or with a 5 to 6 membered heteroaryl group having 1 to 2 heteroatoms selected from O, S, and N, or with a 5 to 6 membered heteroaryl group having 1 to 2 heteroatoms selected from O, S and N and condensed with a phenylgroup, said heteroaryl or condensed heteroaryl group itself substituted with 0-3 R$^1$ groups, or R$^4$ is C(O)(CH$_2$)$_p$COOH, (CH$_2$)$_p$phenyl where the phenyl is substituted with 0-3 R$^1$ groups or with a NO$_2$ group, or R$^4$ is C(O)OC$_1$-C$_6$alkyl, or R$^4$ is CH(CH$_3$) phenyl where the phenyl is substituted with 0-3 R$^1$ groups, or R$^4$ is C(O)(CH$_2$)$_p$phenyl where the phenyl is substituted with 0-3 R$^1$ groups, or R$^4$ is C(O)CH (Ph)$_2$, C(O)—CH$_2$-(3PhO-)Ph, or R$^4$ is a 5 to 6 membered heteroaryl group having 1 to 2 heteroatoms selected from O, S, and N, or a 5 to 6 membered heteroaryl group having 1 to 2 heteroatoms selected from O, S and N and condensed with a phenylgroup, said heteroaryl or condensed heteroaryl group itself substituted with 0-3 R$^1$ groups, or R$^4$ is CH$_2$heteroaryl where the heteroaryl group is 5 or 6 membered and has 1 to 2 heteroatoms selected from O, S, or R$^4$ is SO$_2$-alkyl of 1 to 6 carbons, SO$_2$-Ph where the phenyl is substituted with 0-3 R$^1$ groups or with NO$_2$ or with COOR$^5$ group, or R$^4$ is C(O)NH-alkylphenyl, or C(O)

NH-phenyl where the alkyl group has 1 to 4 carbons and where the phenyl is substituted with 0-3 R$^1$ groups;

p is an integer having the value of 0 to 4;

R$^5$ is alkyl of 1 to 6 carbons or phenyl substituted with 0-3 R$^1$ groups or with an OPh group;

R$^6$ is alkyl of 1 to 6 carbons;

the asterisk indicates an asymmetric carbon, the wavy line represents a bond that can be in the R or in the S configuration, or a pharmaceutically acceptable salt of said compound, with the proviso that compounds selected from the group consisting of compounds identified below with structural formulas and designations of the variables R$^1$

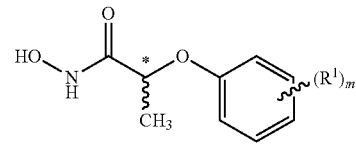

where R$^1$ is 2-Me, 4-Me, 4-Br, 2-phenyl, 2-(3-propenyl), 4-O-n-Bu, 2-Me-4-Br, 2,4-diCl, 2,4-diBr, 2,5-diCl, 2,4,5-triCl, 2,5-diCl-4-Me, 2,4-diCl-4-Br, or 2-Me-4-Cl
and

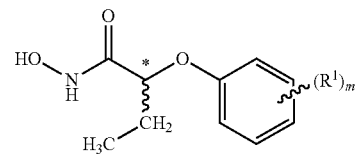

where R$^1$ is 2-phenyl, 2-(3-propenyl), 2,3-dimethyl, or 2,4-diCl,
and

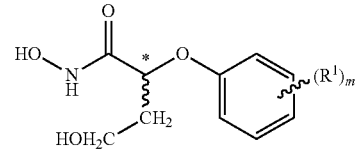

where R$^1$ is 2-Me, 2-Cl, 2-OMe, 3-Me, 3-Cl, 3-OMe, 3-CF$_3$, 4-OMe, 4-SMe, 4-phenyl, 2-COOMe, 3-COOMe or 4-COOEt,
and

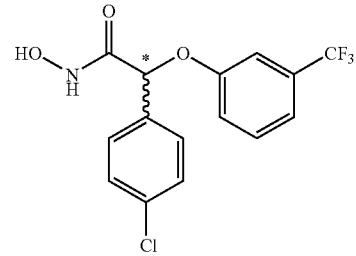

are not included in the claim.

2. A compound in accordance with claim 1 where $R^1$ is selected independently from the group consisting of F, Cl, methyl and methoxy.

3. A compound in accordance with claim 2 where m is an integer having the value of 2 or 3.

4. A compound in accordance with claim 3 where m is 2, one $R^1$ group is methyl in the 3 (meta) position on the phenyl ring, and the other $R^1$ group is fluoro in the 4 (para) position of the phenyl ring.

5. A compound of the formula

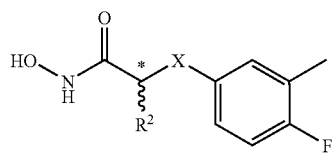

where $R^2$ is H, alkyl of 1 to 6 carbons $(CH_2)_2OH$, or $(CH_2)_4OH$;

the asterisk represents that the adjacent carbon is asymmetric and the wavy line represents a bond which can be of either R or S configuration, or a pharmaceutically acceptable salt of said compound, with the proviso that when $R^2$ is H then the carbon bearing the asterisk is not asymmetric.

6. A compound of the formula

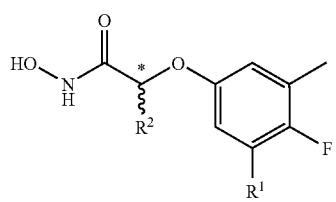

where $R^1$ is H, or alkyl of 1 to 6 carbons;

$R^2$ is $(CH_2)_nNHR^4$, $(CH_2)_nOR^4$, $CH_2)_nN(CH_3)R^4$, $C_{2-6}$alkenyl$OCH_2$phenyl where alkenyl has one double bond and the phenyl group is substituted with 0 to 3 groups selected from methyl and fluoro;

n is an integer selected from 1 to 6;

$R^4$ is $(CH_2)_p$phenyl, $(CH_2)_p$thienyl, $(CH_2)_p$furyl where the phenyl, thienyl and furyl groups are substituted with 0 to 3 groups selected from methyl and fluoro;

p is an integer selected from 1 to 3;

the asterisk represents that the adjacent carbon is asymmetric and the wavy line represents a bond which can be of either R or S configuration, or a pharmaceutically acceptable salt of said compound.

7. A compound in accordance with claim 6 where p is one (1).

8. A compound in accordance with claim 6 where $R^2$ is $(CH_2)_nNHR^4$.

9. A compound in accordance with claim 6 where $R^2$ is $(CH_2)_nOR^4$.

10. A compound in accordance with claim 6 where $R^2$ is $(CH_2)_nN(CH_3)R^4$.

11. A compound in accordance with claim 6 where $R^2$ is $C_{2-6}$alkenyl$OCH_2$phenyl.

12. A compound in accordance with claim 6 where $R^1$ is H.

13. A compound of the formula

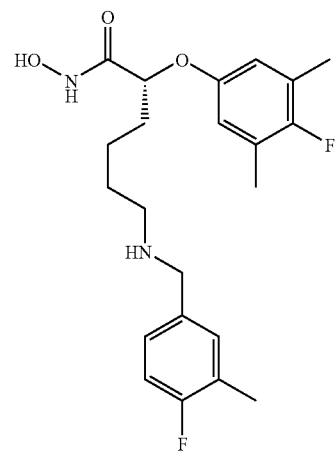

or a pharmaceutically acceptable salt of said compound.

14. A compound of the formula

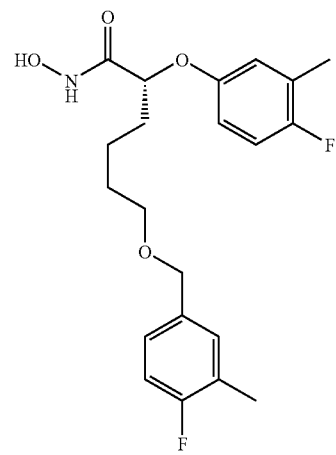

or a pharmaceutically acceptable salt of said compound.

15. A method of treating infection of a mammal by bacillus anthraci by administering to said mammal a pharmaceutical composition containing a pharmaceutically acceptable excipient and one or more compounds defined by formula below

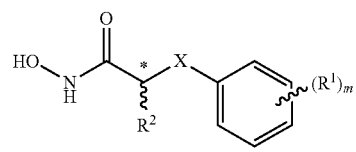

where $R^1$ is F, Cl, Br, I, alkyl of 1-3 carbons, alkoxy of 1-3 carbons, thioalkoxy of 1-3 carbons, phenyl, O-phenyl, CN, $CF_3$, $OCF_3$, OH, $NH_2$, $NHC_1$-$C_6$alkyl, $N(C_1$-$C_6$alkyl$)_2$, COOH or $COO(C_1$-$C_6$alkyl);

m is an integer having the value of 1 to 3;

$R^2$ is alkyl of 1-6 carbons; $C_1$-$C_6$ alkylphenyl where phenyl is substituted with 0-3 $R^1$ groups, $C_2$-$C_6$alkenylO$(CH_2)_n$phenyl where alkenyl has 2 to 6 carbons and one double bond and phenyl is substituted with 0-3 $R^1$ groups, $C_1$-$C_6$ alkylcyclohexyl, $(CH_2)_nOR^3$, $(CH_2)_nNHR^4$, $NR^4C_1$-$C_6$alkyl, $(CH_2)_nCF_3$, $CH_2OCH_2$phenyl; $(CH_2)_nNH(CH_2)_nR^4$, $(CH_2)_nNR^6R^4$, $(CH_2)_nNR^6(CH_2)_n(CH_2)_nO(CH_2)_nR^4$, $(CH_2)_nOR^4$, n is an integer having the value of 1 to 8;

$R^3$ is H, alkyl of 1 to 6 carbons, alkylphenyl where the alkylgroup has 1 to 6 carbons and the phenyl is substituted with 0-3 $R^1$ groups;

$R^4$ is H, cyclohexyl, C(O)alkyl of 1 to 4 carbons, C(O)alkylphenyl where the alkylgroup has 1 to 4 carbons and the phenyl is substituted with 0-3 $R^1$ groups or with a 5 to 6 membered heteroaryl group having 1 to 2 heteroatoms selected from O, S, and N, or with a 5 to 6 membered heteroaryl group having 1 to 2 heteroatoms selected from O, S and N and condensed with a phenylgroup, said heteroaryl or condensed heteroaryl group itself substituted with 0-3 $R^1$ groups, or $R^4$ is C(O)$(CH_2)_p$COOH, $(CH_2)_p$phenyl where the phenyl is substituted with 0-3 $R^1$ groups or with a $NO_2$ group, or $R^4$ is C(O)O$C_1$-$C_6$alkyl, or $R^4$ is $CH(CH_3)$phenyl where the phenyl is substituted with 0-3 $R^1$ groups, or $R^4$ is C(O)$(CH_2)_p$phenyl where the phenyl is substituted with 0-3 $R^1$ groups, or $R^4$ is C(O)CH$(Ph)_2$, C(O)—$CH_2$-(3PhO-)Ph, or $R^4$ is a 5 to 6 membered heteroaryl group having 1 to 2 heteroatoms selected from O, S, and N, or a 5 to 6 membered heteroaryl group having 1 to 2 heteroatoms selected from O, S and N and condensed with a phenylgroup, said heteroaryl or condensed heteroaryl group itself substituted with 0-3 $R^1$ groups, or $R^4$ is $CH_2$heteroaryl where the heteroaryl group is 5 or 6 membered and has 1 to 2 heteroatoms selected from O, S, or $R^4$ is $SO_2$-alkyl of 1 to 6 carbons, $SO_2$-Ph where the phenyl is substituted with 0-3 $R^1$ groups or with $NO_2$ or with $COOR^5$ group, or $R^4$ is C(O)NH-alkylphenyl, or C(O)NH-phenyl where the alkyl group has 1 to 4 carbons and where the phenyl is substituted with 0-3 $R^1$ groups;

p is an integer having the value of 0 to 4;

$R^5$ is alkyl of 1 to 6 carbons or phenyl substituted with 0-3 $R^1$ groups or with an OPh group;

$R^6$ is alkyl of 1 to 6 carbons, the asterisk indicates an asymmetric carbon, the wavy line represents a bond that can be in the R or in the S configuration, or a pharmaceutically acceptable salt of said compound.

16. A method of inhibiting the lethal factor enzyme released by bacillus anthraci in a mammal where such inhibition is needed, said method comprising contacting said enzyme with one or more compounds defined by formula in accordance with claim 15.

17. A method in accordance with claim 16 where said mammal is a human being.

* * * * *